(12) United States Patent
Nabatova-Gabain et al.

(10) Patent No.: US 7,271,901 B2
(45) Date of Patent: Sep. 18, 2007

(54) THIN-FILM CHARACTERISTIC MEASURING METHOD USING SPECTROELLIPSOMETER

(75) Inventors: Nataliya Nabatova-Gabain, Tokyo (JP); Yoko Wasai, Nagoya (JP)

(73) Assignee: Horiba, Ltd., Kyoto (JP)

( * ) Notice: Subject to any disclaimer, the term of this patent is extended or adjusted under 35 U.S.C. 154(b) by 24 days.

(21) Appl. No.: 10/478,499

(22) PCT Filed: May 22, 2002

(86) PCT No.: PCT/JP02/04932

§ 371 (c)(1),
(2), (4) Date: Jun. 12, 2004

(87) PCT Pub. No.: WO02/095372

PCT Pub. Date: Nov. 28, 2002

(65) Prior Publication Data

US 2004/0207844 A1    Oct. 21, 2004

(30) Foreign Application Priority Data

May 22, 2001  (JP)  ............................. 2001-152848
May 22, 2001  (JP)  ............................. 2001-152849
Apr. 24, 2002  (JP)  ............................. 2002-122579

(51) Int. Cl.
*G01J 4/00*    (2006.01)

(52) U.S. Cl. .................................................. 356/369
(58) Field of Classification Search ......... 356/364–369

See application file for complete search history.

(56) References Cited

U.S. PATENT DOCUMENTS

| 4,999,509 A | 3/1991 | Wada et al. |
| 5,889,592 A | 3/1999 | Zawaideh |
| 6,002,485 A * | 12/1999 | Masao ........................ 356/369 |

(Continued)

FOREIGN PATENT DOCUMENTS

JP    1-123135 A    5/1989

(Continued)

OTHER PUBLICATIONS

J.F. Elman et al., "Characterization of biaxially-stretched plastic films by generalized ellipsometry", Thin Solid Films 313-314, (1998), pp. 814-818.

(Continued)

*Primary Examiner*—Tarifur Chowdhury
*Assistant Examiner*—Isiaka O Akanbi
(74) *Attorney, Agent, or Firm*—Venable LLP; Michael A. Sartori; Catherine M. Voorhees

(57) ABSTRACT

The present invention provides a thin film property measuring method using a spectroscopic ellipsometer. With the measuring method, a model including a combination of the film thickness, complex refractive index, or the like, of each layer is formed, and fitting is made for the measured spectra and the spectra calculated based upon the model, with the model and the incident angle being modified over a predetermined number of repetitions, thereby determining the structure, the wavelength dependency of the dielectric constant, and the composition ratio, of a thin film including a compound semiconductor layer on a substrate. Furthermore, new approximate calculation is employed in the present invention, thereby enabling the concentration of the atom of interest contained in polycrystalline compound semiconductor to be calculated.

21 Claims, 14 Drawing Sheets

U.S. PATENT DOCUMENTS

| | | | |
|---|---|---|---|
| 6,128,085 A * | 10/2000 | Buermann et al. | 356/369 |
| 6,268,916 B1 * | 7/2001 | Lee et al. | 356/369 |
| 6,297,880 B1 * | 10/2001 | Rosencwaig et al. | 356/369 |
| 6,320,657 B1 * | 11/2001 | Aspnes et al. | 356/369 |
| 6,384,916 B1 * | 5/2002 | Furtak | 356/369 |
| 6,590,656 B2 * | 7/2003 | Xu et al. | 356/369 |
| 6,657,736 B1 * | 12/2003 | Finarov et al. | 356/625 |
| 6,753,961 B1 * | 6/2004 | Norton et al. | 356/364 |
| 2004/0233432 A1 * | 11/2004 | Akada et al. | 356/364 |

FOREIGN PATENT DOCUMENTS

| | | |
|---|---|---|
| JP | 9-218133 A | 8/1997 |
| JP | 2001-118903 A | 4/2001 |
| JP | 2002-76083 A | 3/2002 |
| JP | 2002-214074 A | 7/2002 |

OTHER PUBLICATIONS

John A. Woollam et al., "Overview of Variable Angle Spectroscopic Ellipsometry (VASE), Part 1: Basic Theory and Typical Applications", Critical Reviews, vol. CR72, Optical Metrology, pp. 2-28.

Readout, No. 21, Sep. 20, 2000, pp. 26 to 30.

Vacuum, vol. 60, No. 4, Mar. 2001, pp. 419 to 424.

Thin Solid Films, 313/314(1998), pp. 124 to 127.

John A. Woollam et al., "Overview of Variable Angle Spectroscopic Ellipsometry (VASE), Part I: Basic Theory and Typical Applications", Critical Reviews, vol. CR72, Optical Metrology, pp. 2-28, Jul. 18, 1999.

H. G. Tompkins, "A User's Guide to Ellipsometry," Academic Press, Inc., 1993, pp. vi-xv, 34-39, 50-51, 82-95, 212-217.

S. Bosch et al, "Effective Dielectric Function of Mixtures of Three or More Materials: a Numerical Procedure for Computations," Surface Science 453, 2000, pp. 9-17.

K. G. Merkel et al., "Characterization of Multilayer GaAs/AlGaAs Transistor Structures by Variable Angle Spectroscopic Ellipsometry," Japanese Journal of Applied Physics, vol. 28, No. 5, 1989, pp. 1118-1123.

B. A. Tirri et al., "Spectroellipsometric Characterization of Inhomogenous Films," SPIE vol. 794, 1987, pp. 252-261.

D. G. Seiler et al, "Characterization and Metrology for ULSI Technology," AIP Conference Proceedings 449, 1998, pp. v-xv, 298-302.

M. Losurdo et al., "In Situ Ellipsometric Monitoring of GaAs Surface Modifications During Plasma Processing: Chemistry and Kinetics," Thin Solid Films 313-314, 1998, pp. 501-504.

C. Pickering et al, "Real-Time Spectroscopic Ellipsometry Monitoring of $Si_{1-x}Ge_x$/Si Epitaxial Growth," J.Va. Sci. Technol. A 13(3), 1995, pp. 740-744.

S. Zollner et al, "Optical Constants and Ellipsometric Thickness Determination of Strained $Si_{1-x}Ge_x$:C Layers on Si (100) and Related Heterostructures," American Institute of Physics, 2000, pp. 4102-4108.

J. M. Leng et al, "Simultaneous Measurement of Six Layers in a Silicon on Insulator Film Stack Using Spectroophotometry and Beam Profile Reflectometry," American Institute of Physics, 1997, pp. 3570-3578.

Excerpts from Chps. 8 and 9 as Well as Protypical Analysis 2, 3, 4, 5, 8 and 9 and Regression of Algorithms of "Spectroscopic Ellipsometry and Reflectometry"; Tompkins et al, John Wiley & Sons, (1999).

"Variable Angle of Incidence Spectroscopic Ellipsometry: Applications to $GaAs-Al_xGa_{1-x}As$ Multiple Hetrostructures" Snyder et al., J. App. Phys. 60(9), Nov. 1986.

"Real-Time Spectral Ellipsometry Applied to Semiconductor Thin Films Diagnosis; Duncan et al, From Semiconductor Characterization: Present and Future Needs", Ed. Bullis, Am., Inst. Phys. (1966).

Characterization of Laser Annealed Polysilicon by Spectroscopic Ellipsometry and Comparison to Other Techniques, Boher, et al., SPIE Intl. Proc. of Soc. for Opt. Eng. vol. 2873.

"Analysis of Cermet Films with Large Metal Packing Fractions"; Aspnes, Phys. Rev. B, vol. 33 No. 2, (1986).

"Characterization of Excimer Laser Annealed Polycrystalline $Si_{1-x}Ge_x$ Alloy Thin Films by X-ray Diffraction and Spectroscopic Ellipsometry"; Yu, et al., J. App. Phys. 83(1), Jan. 1998.

Real-Time Monitoring and Control of Epitaxial Semiconductor Growth in a Production Environment by In Situ Spectroscopic Ellipsometry, Thin Solid Films, Johs et al., pp. 313-314, (1998).

"Refined Model for Spectroscopic Ellipsometry Analysis of $Si_xGe_{1-x}$/Si Straomed Eterjunctiona", Ferrieu, Appl. Phys. Lett. vol. 76, No. 15.

"Ellipsometry, Variable Angle Spectroscopic", Woollam, Wiley Encyclopedia of Electrical and Electronics Engineering, Edited by Webster, John Wiley and Sons, (2000).

P. T. Carline, C. Pickering, D. J. Robbins, W. Y. Leong, A. C. Pitt, A. G. Cullis, Spectroscopic ellipsometry of $Si_{1-x}Ge_x$ epilayers of arbitrary composition $0<x<0.255$, Applied Physics Letters, Feb. 28, 1994, vol. 64, No. 9 pp. 1114-1116.

* cited by examiner

FIG. 3

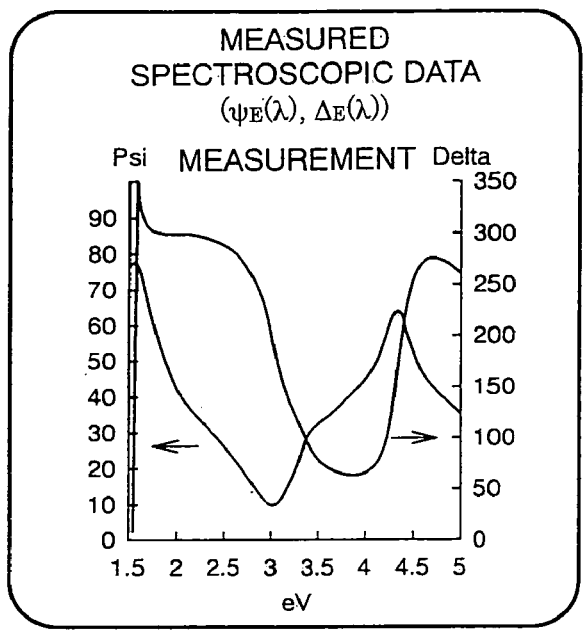

FIG. 4

MODEL IS FORMED SO AS TO SIMULATE THE ACTUAL STRUCTURE OF THE SAMPLE.

- MATERIAL OF THE SUBSTRATE
- THICKNESS (d) OF EACH LAYER
- OPTICAL CONSTANTS OF EACH LAYER ($n, k$ OR $\varepsilon_r, \varepsilon_i$)
- COMPOSITION OF EACH LAYER (EXAMPLE)

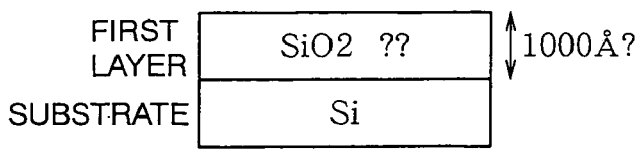

MODEL IS FORMED TAKING THESE ITEMS AS PARAMETERS AND USING AN EXPRESSION WHICH REPRESENTS THE WAVELENGTH DEPENDENCY OF DIELECTRIC CONSTANT (DSP*).

DSP*: DISPERSION FORMULA

......... CALUCULATED SPECTRUM
———— MEASURED SPECTRUM

FIG. 7

FITTING IS PERFORMED FOR d AND THE PARAMETERS OF DSP SO THAT THE DIFFERENCE BETWEEN $(\psi_E(\lambda), \Delta_E(\lambda))$ AND $(\psi_M(\lambda), \Delta_M(\lambda))$ EXHIBITS THE MINIMUM USING THE LEAST SQUARE METHOD.

DETERMINATION IS MADE WHETHER OR NOT THE MODEL SUBJECTED TO FITTING MATCHES THE MEASURED DATA.

FIG. 8

THE MODEL IS MODIFIED BY CHANGING MODEL STRUCTURE OR/AND CHANGING OR ADDING MATERIAL.
(EXAMPLE)

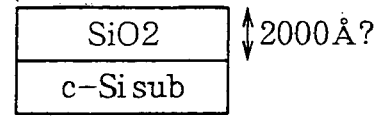
2000Å?

FIG. 9

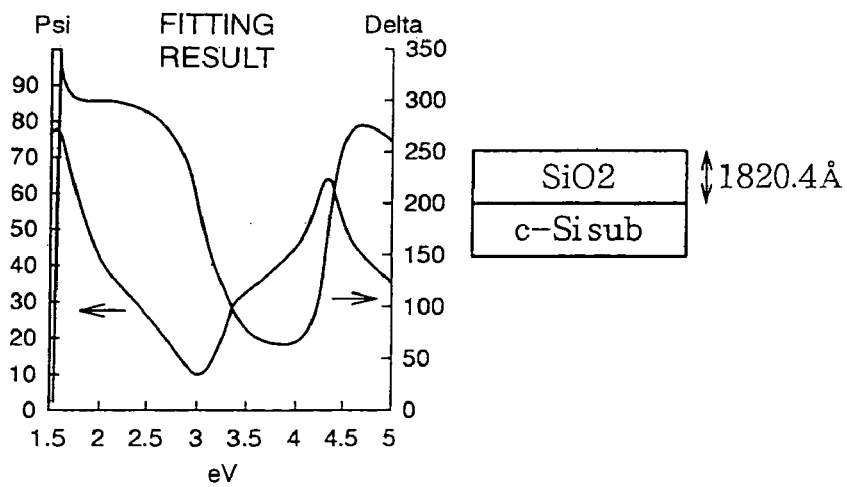

---------- CALCULATED SPECTRUM
———— MEASURED SPECTRUM

FIG.15

FITTING IS PERFORMED FOR d AND THE PARAMETERS OF DSP SO THAT THE DIFFERENCE BETWEEN ($\psi_E(\lambda)$, $\Delta_E(\lambda)$) AND ($\psi_M(\lambda)$, $\Delta_M(\lambda)$) EXHIBITS THE MINIMUM USING THE LEAST SQUARE METHOD.

DETERMINATION IS MADE WHETHER OR NOT THE MODEL SUBJECTED TO FITTING MATCHES THE MEASURED DATA.

FIG.16

THE MODEL IS MODIFIED BY CHANGING MODEL STRUCTURE OR/AND CHANGING OR ADDING MATERIAL.
(EXAMPLE)

| NATIVE OXIDE FILM? | 20Å? |
|---|---|
| SiGe(x=0.2?) | 2000Å? |
| c-Si sub | |

FIG.17

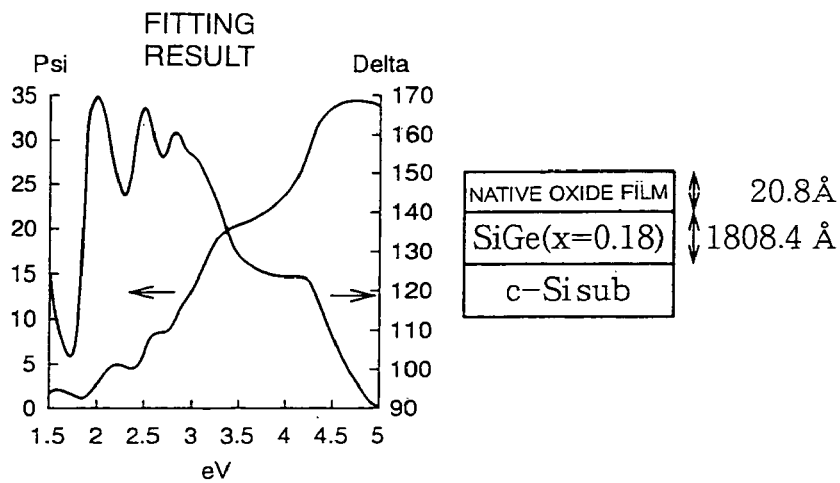

d, n, k, AND COMPOSITION RATIOS ARE OBTAINED.

FITTING RESULT

| NATIVE OXIDE FILM | 20.8Å |
|---|---|
| SiGe(x=0.18) | 1808.4 Å |
| c-Si sub | |

MODEL

| NATIVE OXIDE FILM |
|---|
| $Si_{(1-x)}Ge_x$ |
| Si SUBSTRATE |

| INCIDENT ANGLE | FILM THICKNESS | Ge CONCENTRATION Ge (%) | $\chi^2$ |
|---|---|---|---|
| 74.85 | 1100.4 | 7.7876 | 0.6292 |
| 74.86 | 1100.9 | 7.8474 | 0.5997 |
| 74.87 | 1101.0 | 7.9553 | 0.5727 |
| 74.88 | 1100.9 | 8.0229 | 0.5483 |
| 74.89 | 1100.5 | 8.1347 | 0.5263 |
| 74.90 | 1100.8 | 8.2296 | 0.5067 |
| 74.91 | 1100.6 | 8.3544 | 0.4897 |
| 74.92 | 1100.8 | 8.4480 | 0.4752 |
| 74.93 | 1100.8 | 8.5442 | 0.4632 |
| 74.94 | 1100.7 | 8.6287 | 0.4528 |
| 74.95 | 1100.4 | 8.7327 | 0.4468 |
| 74.96 | 1100.4 | 8.8289 | 0.4424 |
| 74.97 | 1100.3 | 8.9277 | 0.4406 |
| 74.98 | 1099.7 | 9.1162 | 0.4416 |
| 74.99 | 1100.5 | 9.1357 | 0.4445 |
| 75.00 | 1100.2 | 9.2215 | 0.4503 |

THIN-FILM CHARACTERISTIC MEASURING METHOD USING SPECTROELLIPSOMETER

BACKGROUND OF THE INVENTION

1. Field of the Invention

The present invention relates to a thin film property measurement method, particularly to a method for determining the film thickness and optical constants of thin films formed on various types of substrates using a spectroscopic ellipsometer, a method for determining the composition of a crystalline compound semiconductor material, and a method for determining the composition of polycrystalline compound semiconductor material.

2. Description of the Related Art (General Related Art in Spectroscopic Ellipsometry)

A spectroscopic ellipsometer measures the change in polarization between incident and reflected light, and calculates the film thickness (d) and complex refractive index (N=n–ik) from the change in polarization. The change in polarization ($\rho$) is represented by $\rho=\tan \Psi \exp(i\Delta)$, and is dependent upon the parameters such as the wavelength ($\lambda$), the incident angle ($\phi$), the film thickness, the complex refractive index, and accordingly, the relationship between these parameters can be represented by the following expression.

$$(d, n, k) = F(\psi, \Delta, \lambda, \phi)$$

In case of single wavelength ellipsometer, if the incident angle is fixed, only two independent variables of three unknown values of (d, n, k) can be measured, and accordingly, there is the need to fix one of d, n, and k as a known value. Note that in the event that measurement is made with multiple incident angles, the number of measured variables increases, even if the single wavelength ellipsometer is used. However, measured pairs of ($\Psi\phi_i$, $\Delta\phi_i$) corresponding to different incidence angles ($\phi$), are partly correlated, leading to difficulties in obtaining precise values of d, n, and k.

The measured spectrum measured by spectroscopic ellipsometer ($\Psi_E(\lambda_i)$, $\Delta_E(\lambda_i)$), which represents the change in polarization due to reflection from single-layer or multilayer thin films formed on a substrate, includes all information with regard to n and k of the aforementioned substrate, and d, n, and k of each layer. However, the single combination of the information with regard to n and k of the aforementioned substrate, and d, n, and k of each layer, cannot be simply extracted from the aforementioned measured spectra (excluding the case of semi-infinite substrate). In general, the method for extracting of the aforementioned single combination is referred to as "spectroscopic ellipsometry data analysis". During this analysis, modeling is performed using the information with regard to n and k of the aforementioned substrate, and d, n, and k of each layer. The information regarding to n and k of the substrate and each layer included in the model is obtained from reference data (known table data), a dispersion formula, or optical constants of a single-layer thin film from a similar material.

The dispersion formula represents the wavelength-dependency of the dielectric constant of the material, wherein the dielectric constant $\epsilon(\lambda)$ can be determined in the optical range between near infrared light and ultraviolet light based upon the atomic structure of the material. Known examples of dispersion formulas include a formula based on classical physics (a harmonic oscillator), a formula based on quantum mechanics, an empirical formula, and the like, which generally include two or more parameters. The model is applied to the measured data by adjusting all the unknown values (thickness of each layer, parameters of the dispersion formula, volume fractions of material's components, or the like) included in the aforementioned model. This processing is referred to as "fitting", wherein the thickness, parameters of dispersion formula, the volume fractions, and the like, of each layer are obtained. The dielectric constant $\epsilon$ ($\lambda$) of the material can be calculated from the parameters of the dispersion formula, based upon the fitting results. The relation between the dielectric constant of the material and the refractive index is represented by the following expression.

$$\epsilon = N^2$$

Now, brief description will be made regarding fitting operation frequently employed in methods according to the present invention.

(Description Regarding the Fitting Figure of Merit $\chi^2$)

With the set of N pairs of measured (experimental) data as Exp(i=1, 2, and so on through N), and with the set of N pairs of the data calculated using the model as Mod(i=1, 2, and so on through N), making assumption that error of measurement follows normal distribution, and with the standard deviation as $\sigma i$, the mean square error ($\chi^2$) is represented by the expression $$\chi^2 = [1/(2N-P)]\sum_{i=1}^{N}(\text{Exp}-\text{Mod})^2/\sigma_i^2$$

wherein P represents the number of the parameters. The aforementioned expression indicates that the smaller $\chi^2$ is, the better the model matches the measured results. Accordingly, the best model can be selected from multiple models by selecting the model having the smallest $\chi^2$.

The aforementioned change in light polarization is proportional to the volume through which the light passes (The phase angle ($\beta$) multiplied by the area of the beam's cross section). The phase angle ($\beta$) is represented by the following expression $$\beta = 2\pi(d/\lambda)(N^2 - N_A^2 \sin^2\phi_0)^{1/2}$$

wherein $N_A$ and N represent the complex refractive indices of the ambient and substrate respectively.

Making an assumption that the beam's cross section is constant, the change in polarization can be expressed Change in polarization $\propto$ Film thickness (d)×Complex refractive index (n)×f($\phi$)

wherein $\phi$ represents the incident angle.

As can be understood from this expression, in the event that the film thickness (d) and the complex refractive index (N) are small values, the change of the phase angle ($\beta$) becomes small, and the measurement might become difficult.

Furthermore, as can be understood from the aforementioned expression, the precision of the incident angle affects the change in polarization. Accordingly, a method for obtaining a precise incident angle is necessary. That is to say, determination of the precise incident angle allows the precise determination of the change in the polarization of reflected light.

Furthermore, there is great demand for a method for obtaining the precise composition ratio of the compound semiconductor layer, or a method for maintaining the composition ratio in a predetermined range. The complex refractive index N of a compound semiconductor layer $A_{(1-x)}B_x$ is determined, depending on the value of x. For example, in a case of a compound semiconductor layer $A_{(1-x)}B_x$ formed by atoms A and B on the substrate A, and furthermore in the event that the composition ratio x is small, the difference between the ($n_0$, $k_0$) of the substrate and the ($n_j$, $k_j$) of the compound semiconductor layer is almost non-existent, leading to small change in polarization, due to this layer. Accordingly, the inventors of the present invention believe that precise measurement of the incident angle is important (see FIGS. 18 and 19).

Recently, there is great demand for measurement of the concentration or the like of the atoms (atoms of interest) in a desired polycrystalline compound semiconductor layer.

In the present invention, Effective Medium Theory (EMT) is used to calculate the effective dielectric function of materials, those dielectric function's wavelength dependence is difficult or impossible to express, using only one dispersion formula.

In general, the effective dielectric constant ($\epsilon$) of the host material which contains N number of inclusions (guest materials), each inclusion layer enough to possess it's own dielectric constant, is represented by the expression $$(\varepsilon - \varepsilon_h)/(\varepsilon + k\varepsilon_h) = \sum_{j=1}^{N} f_j(\varepsilon_j - \varepsilon_h)/(\varepsilon_j + k\varepsilon_h)$$

wherein $\epsilon_h$ represents the dielectric constant of the host material, $\epsilon_j$ represents the dielectric constant of the j-th guest material, and k represents a screening factor.

Now, let us consider a case in which one cannot distinguish between the host material and the guest material, i.e., a case that materials of comparable amount have been mixed. In this case, approximation can be made wherein the dielectric constant of the host material and the effective dielectric constant of mixed material are the same $\epsilon_h = \epsilon$, therefore $\epsilon_h$ in the aforementioned expression is replaced by the effective dielectric constant $\epsilon$. The aforementioned approximation is called "Bruggeman Effective Medium Approximation", which will be simply referred to as "EMA" in this specification hereafter. Using the EMA, the effective dielectric constant $\epsilon$ of a material, wherein three spherical components a, b, and c have been uniformly mixed, is obtained by the expression $$f_a(\epsilon_a-\epsilon)/(\epsilon_a+2\epsilon)+f_b(\epsilon_b-\epsilon)/(\epsilon_b+2\epsilon)+f_c(\epsilon_c-\epsilon)/(\epsilon_c+2\epsilon)=0$$

wherein $\epsilon$ represents the effective dielectric constant which is to be obtained, $\epsilon_a$, $\epsilon_b$, and $\epsilon_c$, represent the dielectric constants of the spherical components a, b, and c, respectively, and $f_a$, $f_b$, and $f_c$, represent the volume fraction of the corresponding components. Volume fraction will be referred to as "Vf", hereafter. Note that $f_a+f_b+f_c=1$.

Effective Medium Approximation (EMA) is applicable, if the separate regions (components) of mixed material are small compared to the wavelength of light. EMA is used to model thin film on substrate, if this film is either microscopically inhomogeneous or discontinuous or formed by several physically mixed materials.

Now, description will be made regarding a case that materials a, b, and c have been mixed. In this case, EMA is used to calculate the dielectric constant of the mixed layer from the volume fractions of each component and the dielectric constants of corresponding materials a, b and c. Dielectric constant of each component can be determined by either reference data or dispersion formula. Assuming the mixed layer thickness, model can be built and fitted to the measured data.

Crystalline material as used here means a single crystal, which can be regarded as being formed of a single infinite grain (having no grain boundary). On the other hand, actual polycrystalline material is formed of a great number of single crystals (grains), or a great number of grains and amorphous components (material may contain cavities depending on the manufacturing method). To facilitate description, in general, polycrystalline material can be regarded as a mixture of the crystalline and the amorphous components, or a mixture of the crystalline, amorphous, and void components. Accordingly, the dielectric constant of the polycrystalline material can be calculated using the aforementioned EMA.

Dielectric constants are well known for various crystalline materials, and in general, known data (reference) is used. On the other hand, the dielectric constant of the amorphous material is greatly influenced by the manufacturing method, and accordingly, reference data exists and can be used only for limited materials manufactured by limited number of methods.

With the polycrystalline material, the size of grains, the size of grain boundaries, the presence or absence of the amorphous component, and the crystallization ratio have a great influence upon the dielectric constant thereof. Accordingly, reference exists and can be used only for limited materials manufactured by limited number of methods.

For materials which are commonly employed in the semiconductor industry, such as silicon, reference exists and can be used not only for crystalline silicon (c-Si), but also for amorphous silicon (a-Si) and polysilicon (p-Si).

Dielectric constant reference exists and can be also used for crystalline SiGe (c-$Si_{1-x}Ge_x$), which has recently come into great demand, with various Ge concentrations (x). The dielectric constant of the crystalline SiGe (c-$Si_{1-x}Ge_x$) is dependent on the Ge concentration, and accordingly, the Ge concentration can be calculated by obtaining the dielectric constant of the c-SiGe from the spectroscopic ellipsometry data.

On the other hand, polycrystalline SiGe (p-$Si_{1-x}Ge_x$) can have not only various Ge concentrations but also various crystallization ratios, as described above. Accordingly, the dielectric constant of the polycrystalline SiGe (p-$Si_{1-x}Ge_x$) is influenced by the Ge concentration and the crystallization ratio thereof. Thus, it is difficult to make a reference for the polycrystalline SiGe (p-$Si_{1-x}Ge_x$).

As described above, the Ge concentration of p-SiGe cannot be calculated based upon the dielectric constant calculated from spectroscopic ellipsometry data using a reference in the same way as with c-SiGe described above.

SUMMARY OF THE INVENTION

Accordingly, it is a first object of the present invention to provide a thin film measurement method using spectroscopic ellipsometry for determining the thin film structure by building a model including a combination of a film thickness, complex refractive index, and the like, by calculating the simulation spectra, and by performing fitting with regard to the simulation spectra and the measured spectra.

It is a second object of the present invention to provide a composition-determining method for a compound semiconductor layer on a substrate for determining thin film structure and the composition ratio by building a model including a combination of a film thickness, complex refractive index, and the like, of the compound semiconductor layer, by calculating the simulation spectra, and by performing fitting with regard to the simulation spectra and the measured spectra taking the incident angle as a parameter.

It is a third object of the present invention to provide a measurement method for calculating the concentration of the atoms of interest in polycrystalline compound semiconductor based upon ellipsometry data using a new approximation calculation.

In order to achieve the aforementioned first object, the present invention provides a measuring method for a thin film on a substrate which is to be measured, using a spectroscopic ellipsometer which comprises a spectrum measuring step for obtaining spectra $\Psi_E(\lambda_i)$ and $\Delta_E(\lambda_i)$ by measuring a thin film on a substrate which is to be measured with various wavelengths of incident light, which represent the change in polarization of the incident light and the reflected light for each wavelength $\lambda_i$, a modeling spectrum calculating step wherein a model including the substrate with ($N_0(n_0, k_0)$), a first layer with ($d_1, N_1(n_1, k_1)$), and a j-th layer with ($d_j, N_j(n_j, k_j)$), is formed, and modeling spectra $\Psi_M(\lambda_i)$ and $\Delta_M(\lambda_i)$ are obtained based upon the model using reference data or a dispersion formula, a comparative evaluating step wherein comparison is made between the measured spectra $\Psi_M(\lambda_i)$ and $\Delta_E(\lambda_i)$ and the modeling spectra $\Psi_M(\lambda_i)$ and $\Delta_M(\lambda_i)$, and the structure corresponding to the modeling spectra $\Psi_M(\lambda_i)$ and $\Delta_M(\lambda_i)$ satisfying predetermined evaluation criteria is determined as the measured result, and a modifying step wherein the model not satisfying the predetermined evaluation criteria is modified, and processing in the modeling spectrum calculating step and processing in the comparative evaluating step are performed again.

Evaluation of the model may be performed with an evaluation criterion wherein the mean square error of the measured spectra $\Psi_E(\lambda_i)$ and $\Delta_E(\lambda_i)$ and the modeling spectra $\Psi_M(\lambda_i)$ and $\Delta_M(\lambda_i)$ is obtained for each model, and the model with the minimal mean square error is determined to be the best model.

Simulation spectra $\Psi_{Mk}(\lambda_i)$ and $\Delta_{Mk}(\lambda_i)$ may be calculated with an incident angle $\phi_k$ as a parameter around the nominal incident angle $\phi_0$ used in the spectrum measuring step, in the model simulation spectrum calculating step, and a comparison may be made between the measured spectra $\Psi_E(\lambda_i)$ and $\Delta_E(\lambda_i)$ and the modeling spectra $\Psi_{Mk}(\lambda_i)$ and $\Delta_{Mk}(\lambda_i)$, and the structure corresponding to the modeling spectra $\Psi_{Mk}(\lambda_i)$ and $\Delta_{Mk}(\lambda_i)$ satisfying predetermined evaluation criteria may be determined as the measured result in the comparative evaluating step.

In order to achieve the aforementioned second object, the present invention provides a composition determining method for a compound semiconductor layer wherein the surface of a compound semiconductor layer formed on a substrate is measured using a spectroscopic ellipsometer, and the composition ratios x and y of the compound semiconductor layer formed on the substrate are determined, the composition determining method which comprises a spectrum measuring step for obtaining spectra $\Psi_E(\lambda_i)$ and $\Delta_E(\lambda_i)$ by measuring a thin film on a substrate which is to be measured with various wavelengths of incident light, which represent the change in polarization of the incident light and the reflected light for each wavelength $\lambda_i$, a modeling spectrum calculating step wherein a model including the substrate with ($N_0(n_0, k_0)$), and j-th layers with ($d_j, N_j(n_j, k_j)$), is formed, and modeling spectra $\Psi_M(\lambda_i)$ and $\Delta_M(\lambda_i)$ are obtained based upon the model, a comparative evaluating step wherein comparison is made between the measured spectra $\Psi_M(\lambda_i)$ and $\Delta_E(\lambda_i)$ and the modeling spectra $\Psi_M(\lambda_i)$ and $\Delta_M(\lambda_i)$, and the structure corresponding to the modeling spectra $\Psi_M(\lambda_i)$ and $\Delta_M(\lambda_i)$ satisfying predetermined evaluation criteria is determined as the measured result (d, n, k, and the composition ratio are determined), and a modifying step wherein the model not satisfying the predetermined evaluation criteria is modified, and processing in the modeling spectrum calculating step and processing in the comparative evaluating step are performed again.

Evaluation of the model may be performed with an evaluation criterion wherein mean square error of the measured spectra $\Psi_E(\lambda_i)$ and $\Delta_E(\lambda_i)$ and the modeling spectra $\Psi_M(\lambda_i)$ and $\Delta_M(\lambda_i)$ is obtained for each model, and the model with the minimal mean square error is determined to be the best model.

Simulation spectra $\Psi_{Mk}(\lambda_i)$ and $\Delta_{Mk}(\lambda_i)$ may be calculated with an incident angle $\phi_k$ as a parameter around the nominal incident angle $\phi_0$ used in the spectrum measuring step, in the model simulation spectrum calculating step, and wherein a comparison may be made between the measured spectra $\Psi_E(\lambda_i)$ and $\Delta_E(\lambda_i)$ and the modeling spectra $\Psi_{Mk}(\lambda_i)$ and $\Delta_{Mk}(\lambda_i)$, and the structure corresponding to the modeling spectra $\Psi_{Mk}(\lambda_i)$ and $\Delta_{Mk}(\lambda_i)$ satisfying predetermined evaluation criteria may be determined as the measured result in the comparative evaluating step.

The composition determining processing may be performed for a compound semiconductor layer formed of SiGe, AlGaAs, InGaAsP, InGaAs, InAlAs, InGaP, AlGaInP, AlGaInAs, AlGaAsSb, InAsSb, HgCdTe, ZnMgSSe, ZnSSe, ZnCdSe, ZnMnSe, ZnFeSe, or ZnCoSe.

In order to achieve the aforementioned third object, the present invention provides a composition determining method for polycrystalline compound semiconductor using a spectroscopic ellipsometer, which comprises a spectrum measuring step for obtaining spectra $\Psi_E(\lambda_i)$ and $\Delta_E(\lambda_i)$ by measuring the polycrystalline compound semiconductor layer with various wavelengths of incident light, which represent the change in polarization of the incident light and the reflected light for each wavelength $\lambda_i$, and a first analyzing stage including a first step for forming multiple models including the substrate with the complex refractive index of ($N_0(n_0, k_0)$) and layers with the complex refractive indexes of ($N_1 (n_1, k_1)$), ($N_2 (n_2, k_2)$), and so on, and with film thicknesses, wherein the complex refractive index of the polycrystalline compound semiconductor layer is calculated based upon an assumption that the polycrystalline compound semiconductor layer is formed of the mixture of crystalline compound semiconductor containing the atom of interest, amorphous compound semiconductor containing the atom of interest, and crystalline compound semiconductor not containing the atom of interest, a second step for obtaining parameters of a dispersion formula for the unknown amorphous compound semiconductor by performing fitting with the film thicknesses and the volume fraction as variables, a third step for selecting the result with the minimal mean square error and the minimal volume fraction of the amorphous compound semiconductor from the fitting results, and a fourth step for selecting the result with the minimal mean square error and the minimal volume fraction of the amorphous compound semiconductor from the best results from a plurality of models.

The analyzing step may include the above-described first analyzing stage, a second analyzing stage including a first step for obtaining the film thickness and the volume fraction of the polycrystalline compound semiconductor layer or other layers by performing fitting based upon the best model obtained in the step 4 in the first analyzing stage, a second step for evaluating the fitting results, and a third step for storing the evaluated results, and a calculating step for calculating the composition of the atom of interest based upon the volume fraction of the polycrystalline compound semiconductor layer and the composition ratio of the atom of interest contained in the polycrystalline compound semiconductor layer.

Making an assumption that the polycrystalline compound semiconductor layer is formed of the mixture of a crystalline component (known reference data can be used) and an amorphous component, the composition ratio of the polycrystalline compound semiconductor may be obtained based upon the composition ratio and the volume fraction of the corresponding crystalline component, more specifically, making an assumption that the polycrystalline compound semiconductor layer is formed of two kinds of crystalline compound semiconductor a1 and a2, which contain two kinds of atoms P and Q with different composition ratios (X) of the atom of interest Q, and one kind of amorphous compound semiconductor b containing the atom of interest Q, i.e., the polycrystalline compound semiconductor layer is formed of a1 formed of $P_{(1-x1)}Q_{x1}$ with the volume fraction of $Vf_1$, a2 formed of $P_{(1-x2)}Q_{x2}$ with the volume fraction of $Vf_2$, and b formed of R with the volume fraction $Vf_3$, the concentration of the atom of interest contained in the polycrystalline compound semiconductor may be calculated in a concentration calculation step with the expression {Concentration of the atom of interest contained in polycrystalline compound semiconductor=
$(X1 \cdot Vf_1 + X2 \cdot Vf_2) \cdot 100/(Vf_1 + Vf_2)$[atomic %]}.

Approximate calculation may be performed making an assumption that the composition ratio of the amorphous component of the polycrystalline compound semiconductor is the same as the effective composition ratio of the crystalline component thereof.

The a1 may represent crystalline SiGe with Ge concentration of x1 ($Si_{(1-x1)}Ge_{x1}$) and with the volume fraction of $Vf_1$, the a2 may represent crystalline SiGe with Ge concentration of x2 ($Si_{(1-x2)}Ge_{x2}$) and with the volume fraction of $Vf_2$, and the b may represent amorphous SiGe with the volume fraction of $Vf_3$.

The aforementioned composition determining method may further comprise a spectrum measuring step for obtaining spectra $\Psi_E(\lambda_i)$ and $\Delta_E(\lambda_i)$ by measuring the polycrystalline compound semiconductor layer on a substrate which is to be measured with various wavelengths of incident light, which represent the change in polarization of the incident light and the reflected light for each wavelength $\lambda_i$, and a second step wherein processing up to the first step of the above-described second analyzing stage described is performed for multiple measurement conditions (Zi) which can be anticipated, and the model with the minimal mean square error, or the model with the minimal mean square which is in a predetermined range between the predetermined minimal and maximal values of the film thickness, parameters of the dispersion formula, volume fraction, or incident angle, is selected from the results obtained for the multiple measurement conditions.

The mean square errors of the fitting results and measured values may be obtained, and the minimal mean square error, or the minimal mean square error of which the corresponding value is in a predetermined range between the predetermined minimal and maximal values of the film thickness, parameters of the dispersion formula, volume fraction, or incident angle, may be selected as the minimal mean square error value in steps for selecting the result with the minimal error in the above-described first and second analyzing stages.

Thus, the present invention provides the semiconductor industry and others with a thin film property measuring method using a spectroscopic ellipsometer for precisely measuring the properties of a thin film such as the thickness, composition, optical constants, and so forth.

BRIEF DESCRIPTION OF THE DRAWINGS

FIG. 3 is a chart which shows measured spectroscopic data obtained in Step 20 of the thin film measuring method;

FIG. 4 is a diagram for describing data of a model which is set in Step 21 of the thin film measuring method;

FIG. 7 is a diagram for describing fitting performed in Step 24 of the thin film measuring method;

FIG. 8 is a diagram for describing alternation of the model performed in Step 25 of the thin film measuring method;

FIG. 9 shows a chart showing the data obtained based upon the determined model, and a diagram illustrating the determined structure, for describing Step 26 of the thin film measuring method;

FIG. 15 is a diagram for describing fitting performed in Step 24 of the composition determining method;

FIG. 16 is a diagram for describing alternation of a model performed in Step 25 of the composition determining method;

FIG. 17 shows a chart showing the data based upon the determined model, and a diagram illustrating the determined structure, for describing Step 26 of the composition determining method;

DESCRIPTION OF THE PREFERRED EMBODIMENTS

Description will be made below regarding embodiments of the present invention with reference to the drawings.

Figure 1:
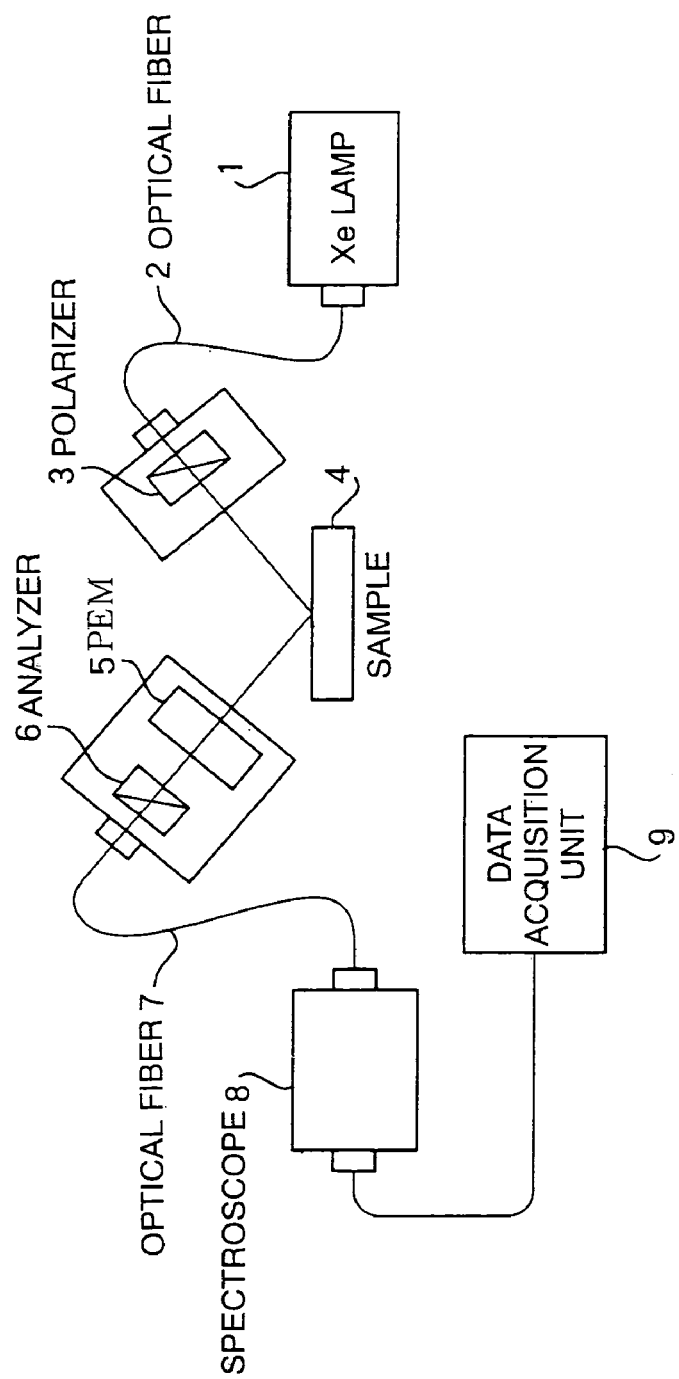
FIG. 1 is a block diagram which illustrates a configuration of an ellipsometer used in the present invention.

FIG. 1 is a block diagram which illustrates a configuration of an ellipsometer employed for a method according to the present invention. The spectroscopic ellipsometer shown in the block diagram performs a spectroscopic measurement step 10 to obtain the measured spectroscopic data described later.

A Xe lamp 1 is a so-called white light source for emitting light containing a great number of wavelength components. The light emitted from the Xe lamp 1 is introduced to a polarizer 3 through an optical fiber 2. The light polarized by the polarizer 3 is cast onto the surface of a sample 4 which is to be measured with a predetermined incident angle (e.g., $\phi=75°$). The reflected light from the sample 4 is introduced to an analyzer 6 through a photo-elastic modulator (PEM) 5. The reflected light is subjected to phase modulation with a frequency of 50 kHz by the photo-elastic modulator (PEM) 5. As a result the polarization of the reflected light, which is originated from the linearly polarized incident light, will change periodically from linearly to elliptically. Accordingly, $\Psi$ and $\Delta$ can be determined within several msec. The output from the analyzer 6 is connected to a spectroscope 8 through an optical fiber 7. The output data from the spectroscope 8 is acquired by a data acquisition unit 9, whereby the spectroscopic measurement step 10 to obtain the measured spectroscopic data ends. Note that the PEM 5 may be situated in front of the polarizer 3 or the analyzer 6.

(Description Regarding a Thin Film Measuring Method According to the Present Invention)

Figure 2:
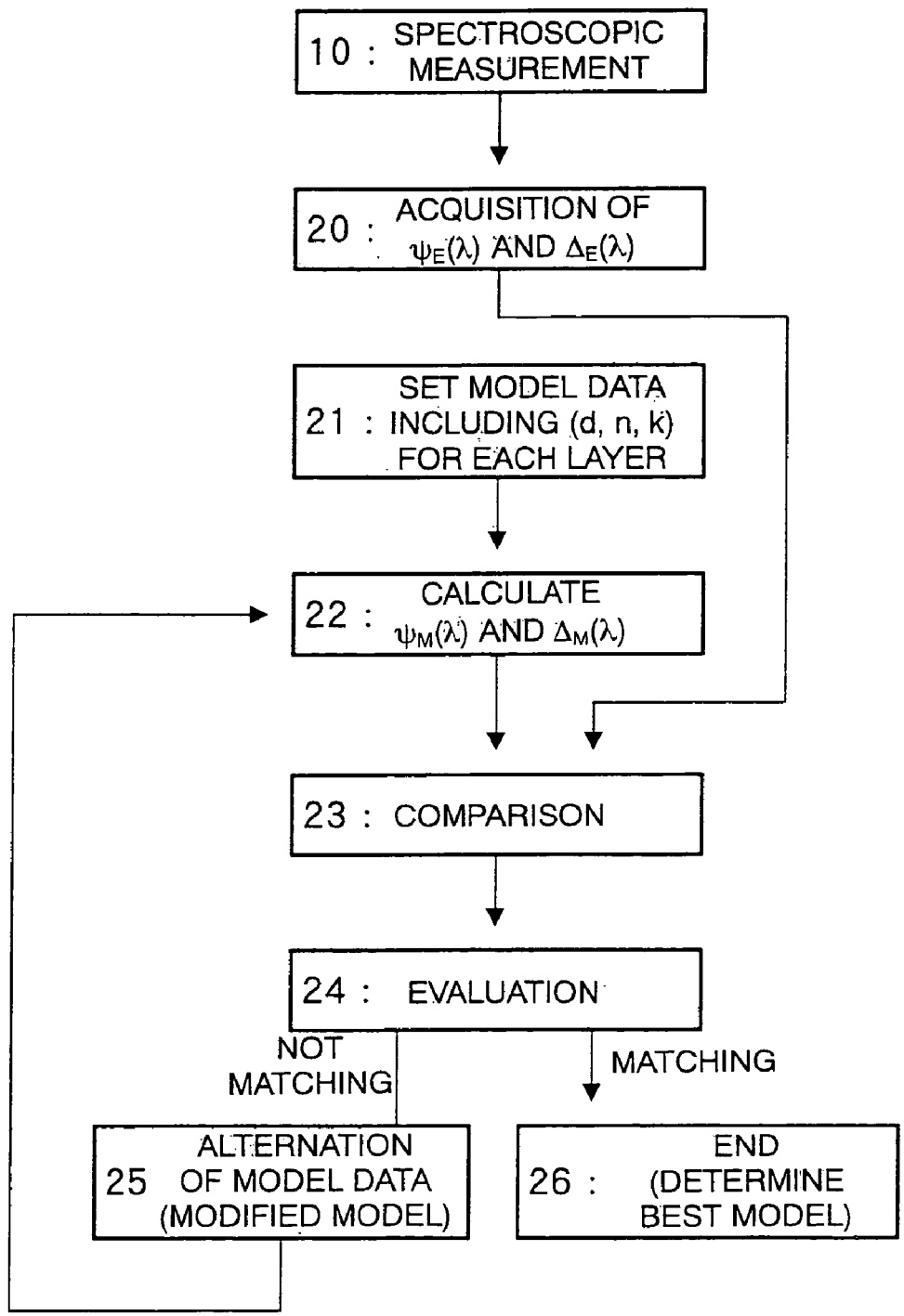
FIG. 2 is a flowchart for describing a thin film measuring method according to the present invention.

FIG. 2 is a flowchart which shows a thin film measuring method using a spectroscopic ellipsometer according to the present invention.

(Step 20)

In Step 20, comparative data is formed based upon the measured spectroscopic data. That is to say, the measured spectroscopic data acquired in Step 10 (spectroscopic measurement step to obtain measured spectroscopic data) is converted into the comparative data in the form of $\Psi_E(\lambda_i)$ and $\Delta_E(\lambda_i)$.

FIG. 3 is a chart showing an example of the measured spectroscopic data acquired in Step 20. The vertical axis represents the measured spectra $\Psi_E(\lambda_i)$ and $\Delta_E(\lambda_i)$.

(Step 21)

In Step 21, modeling is performed for a material which is to be measured with spectroscopic ellipsometer. FIG. 4 is a diagram for describing data of a model formed in Step 21. The model is formed, taking into consideration the manufacturing process or the like for the sample which is to be measured of which the measured data has been converted into the comparative data in the aforementioned Step 20. Setting is made for the optical constants, composition, and film thickness (d), of the substrate and each layer. In the present embodiment, making assumption that the first layer is $SiO_2$ with the film thickness d of 1000 Å deposited on the Si substrate, and setting is performed for the optical constants (n, k or $\epsilon_r$, $\epsilon_i$) of the substrate and the first layer $SiO_2$. Note that known values are used for the optical constants, and the values are modified as appropriate using previously accumulated data.

(Step 22)

Figure 5:
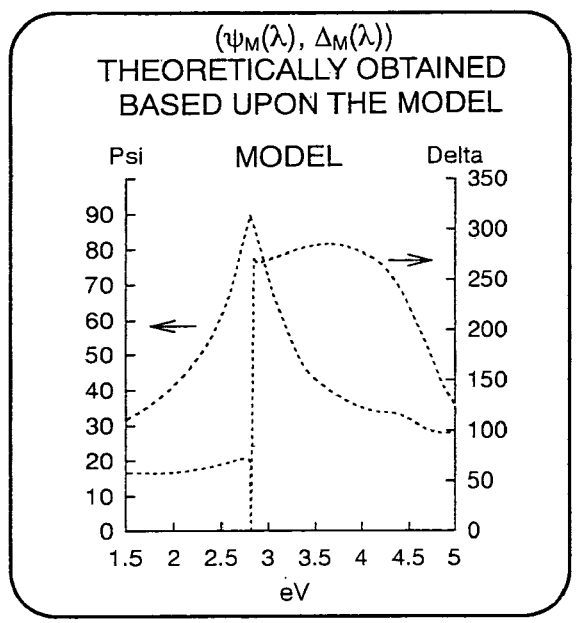
FIG. 5 is a chart which shows obtained data based upon the model used in Step 22 of the thin film measuring method.

In Step 22, modeling spectra are formed as a comparative data based upon the simulation model formed in the above-described Step 21 using the dispersion formula. FIG. 5 is a chart which shows the data from the model calculated in Step 22. The vertical axis and the horizontal axis are the same as described in FIG. 3. As described above, the modeling spectra are formed based upon the model employed in Step 21 using the dispersion formula. The dispersion formula represents the wavelength-dependency of the material, and accordingly, n and k, or $\epsilon_r$ and $\epsilon_i$ can be calculated based thereupon for each wavelength. Subsequently, the modeling spectra are formed by calculating $\Psi_M(\lambda_i)$ and $\Delta_M(\lambda_i)$ from the calculated n and k, or $\epsilon_r$ and $\epsilon_i$, and the thickness d of the aforementioned first layer.

(Step 23)

Figure 6:
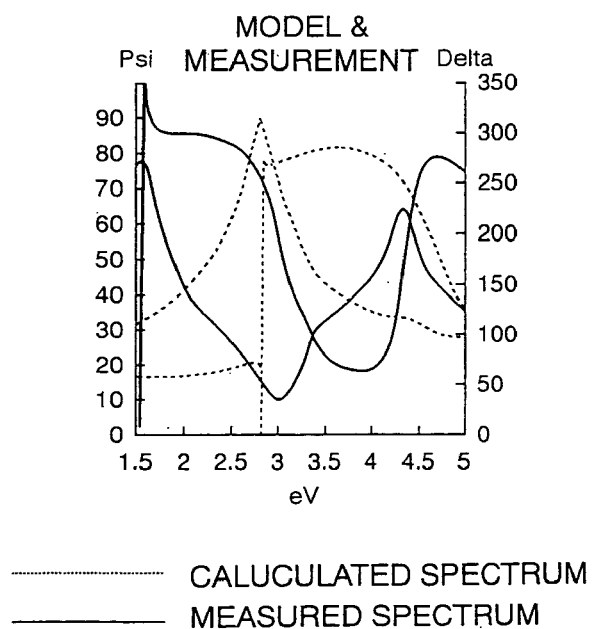
FIG. 6 is a chart wherein measured spectroscopic data which is to be compared in Step 23 of the thin film measuring method and the data obtained based upon the model are superimposed.

In Step 23, a comparison is made between the measured spectroscopic data and the modeling comparative data. FIG. 6 is a chart wherein the measured spectroscopic data and the modeling data, which are to be compared in Step 23, are superimposed. That is to say, the modeling spectra $\Psi_M(\lambda_i)$ and $\Delta_M(\lambda_i)$ calculated in Step 22 and the measured spectrum $\Psi_E(\lambda_i)$ and $\Delta_E(\lambda_i)$ obtained in Step 20 are compared.

(Step 24)

In Step 24, evaluation is made for the above-described comparison results. FIG. 7 is a diagram for describing fitting performed in Step 24. In this step, determination is made whether or not the measured data matches the model based upon the results of fitting parameters wherein parameters are adjusted so that the difference becomes minimal between $(\Psi_E(\lambda_i), \Delta_E(\lambda_i))$ and $(\Psi_M(\lambda_i), \Delta_M(\lambda_i))$ using the least square method. Evaluation is made as follows. First, determination is made whether or not the aforementioned mean square error $(\chi^2)$ of the model is within a predetermined range, or determination is made which $\chi^2$ of models obtained in Step 24 included in finite repeated looping including Step 25 (Step 22→Step 23→Step 24→Step 25→Step 22) described later is minimal. Subsequently, the model corresponding to the determination is selected as the model which matches the measured data.

(Step 25)

FIG. 8 is a diagram for describing alternation of the model in Step 25. In Step 25, in the event that determination has been made that the model does not match the measured spectroscopic data in Step 24, the model is modified to be evaluated as a new model. In this example, the film thickness of the $SiO_2$ layer set in Step 21 is changed from 1000 Å to 2000 Å. Furthermore, the optical constants, composition, or the like of each layer are changed as appropriate, whereby the next model is determined.

(Step 22)

In Step 22, the next $\Psi_M(\lambda_i)$ and $\Delta_M(\lambda_i)$ are theoretically obtained based upon the model set in Step 25. The processing of Step 23, Step 24, Step 25, and Step 22, is repeatedly performed.

(Step 26)

FIG. 9 is a diagram which shows a chart of $\Psi_M(\lambda_i)$ and $\Delta_M(\lambda_i)$ calculated from the fitted parameters (with result thickness and dispersion formula parameters) and a structure with regard to the determined model for describing Step 26.

In Step 26, the data of the model determined to match the measured data in the above-described Step 24 is determined as the measurement results, and represents the end of measurement. In this example, the model with the $SiO_2$ film thickness of 1820.4 Å is determined from the model's set in the above-described repeated processing, having exhibited the minimal $\chi^2$.

Next, description will be made regarding a case wherein measurement is made taking the incident angle around the nominal incident angle $\phi_0$ as a parameter. As described above, the change in polarization ($\rho$) is represented by $\rho = \tan\Psi \exp(i\Delta)$, and is dependent upon the parameters such as the wavelength ($\lambda$), the incident angle ($\phi$), the film thickness, the complex refractive index, and the like, and the relationship between these parameters can be represented by the following expression.

$$(d, n, k) = F(\Psi, \Delta, \lambda, \phi)$$

It is anticipated that a model with the incident angle $\phi_0$ minutely modified matches the measured data better than the model with the nominal incident angle $\phi_0$ shown in FIG. 1, due to minute roughness of the sample surface. Accordingly, it is reasonable to think that the above-described $\Psi_E(\lambda_i)$ and $\Delta_E(\lambda_i)$ have been measured with the incident angle modified from $\phi_0$.

That is to say, with the thin film measurement method using the aforementioned spectroscopic ellipsometer, measurement is made as follows. First, the above-described $\Psi_E(\lambda_i)$ and $\Delta_E(\lambda_i)$ are obtained by the measurement with the nominal incident angle $\phi_0$. In the above-described model simulation spectrum calculation step for obtaining the above-described $\Psi_M(\lambda_i)$ and $\Delta_M(\lambda_i)$, the simulation spectra $\Psi_{M0}(\lambda_i)$ and $\Delta_{M0}(\lambda_i)$ with the incident angle as the nominal incident angle $\phi_0$, and the simulation spectra $\Psi_{Mk}(\lambda_i)$ and $\Delta_{Mk}(\lambda_i)$ with the incident angle $\phi_k$ around the nominal incident angle $\phi_0$ are obtained. The obtained simulation spectra calculated in Step 21 are compared to $\Psi_E(\lambda_i)$ and $\Delta_E(\lambda_i)$.

In this example, in Step 21, multiple models are built for one combination of (d, n, k) with incident angles around the aforementioned nominal incident angle $\phi_0$ of 75.00°, e.g., angles ... 74.8°, ... 75.0°, ... 75.2° and so forth. In the same way, multiple models are formed for other combinations of (d, n, k) with incident angles around the aforementioned nominal incident angle $\phi_0$, e.g., angles ... 74.8°, ... 75.0°, ... 75.2° and so forth. The combination exhibiting the minimal $\chi^2$ is selected from the aforementioned combinations as the best model through Step 24.

As described above in detail, with the thin film measurement method using a spectroscopic ellipsometer according to the present invention, the thin film structure which has been difficult to measure can be measured with better precision and in a sure manner by using modeling, and furthermore by performing fitting of the incident angle.

(Description Regarding a Composition Determining Method for a Compound Semiconductor Layer on a Substrate According to the Present Invention)

Figure 10:
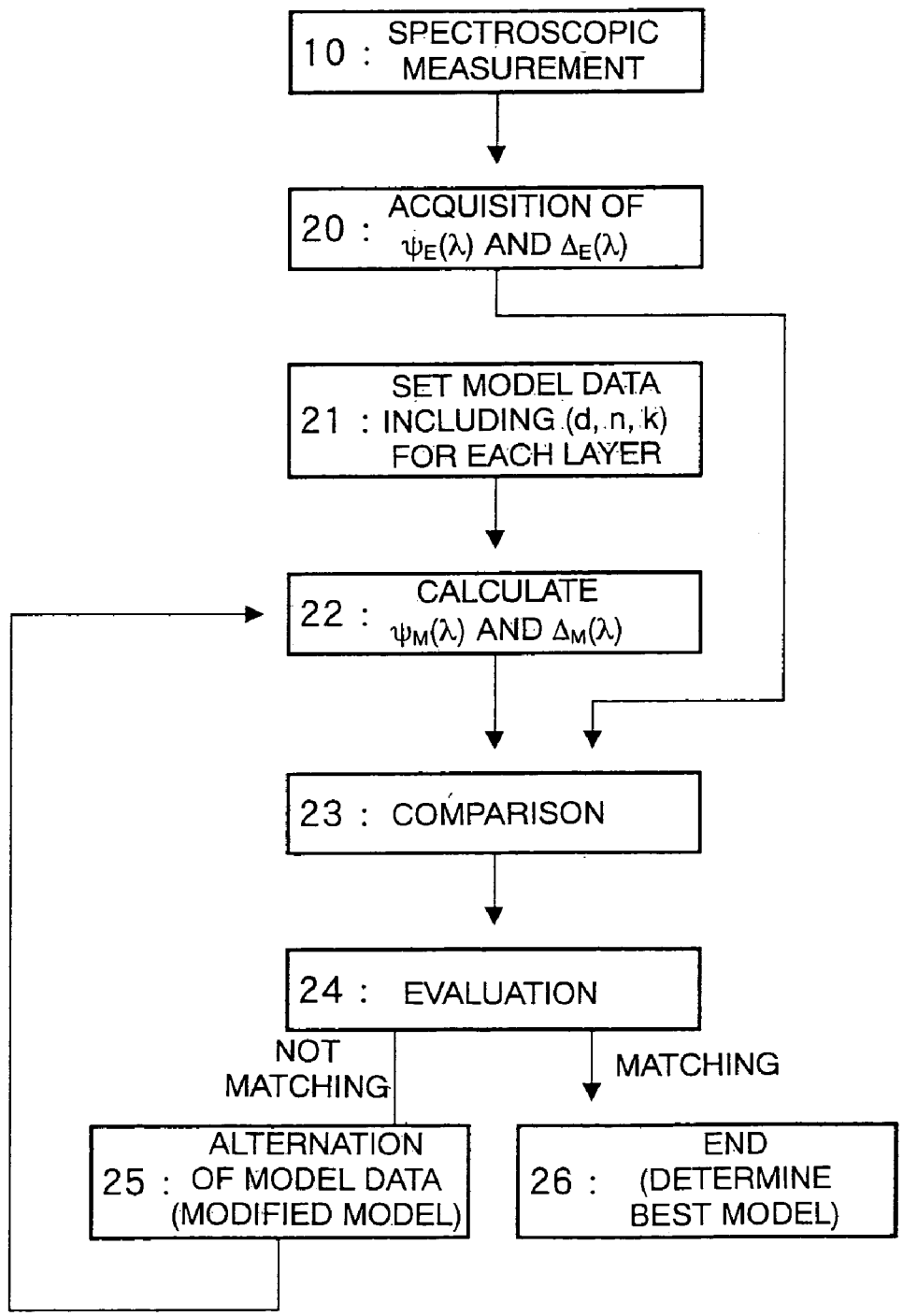
FIG. 10 is a flowchart for describing a composition determining method for compound semiconductor according to the present invention.

FIG. 10 is a flowchart which shows a composition determining method for a compound semiconductor layer on a substrate using a spectroscopic ellipsometer according to the present invention.

(Step 20)

In Step 20, the measured spectroscopic data is converted into comparative data. That is to say, the measured spectroscopic data acquired in the previous Step 10 is converted into the comparative data in the form of $\Psi_E(\lambda_i)$ and $\Delta_E(\lambda_i)$.

Figure 11:
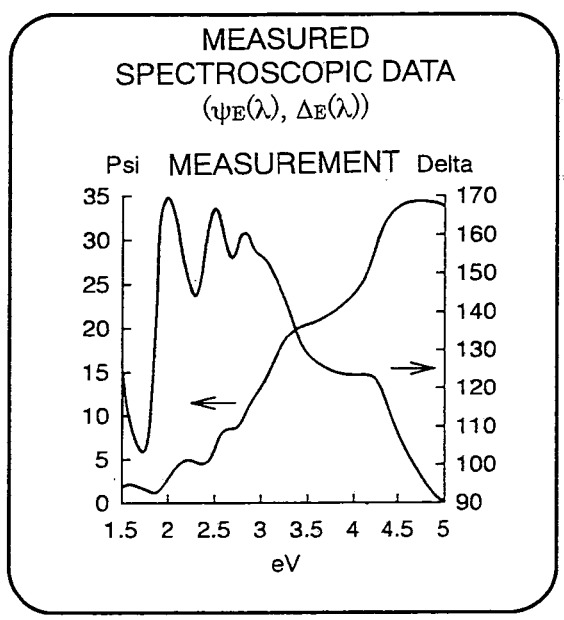
FIG. 11 is a chart which shows measured spectroscopic data obtained in Step 20 of the composition determining method.

FIG. 11 is a chart which shows the measured spectroscopic data obtained in Step 20. The vertical axis represents the measured spectra $\Psi_E(\lambda_i)$ and $\Delta_E(\lambda_i)$ which represents the change in polarization of the reflected light.

(Step 21)

Figure 12:
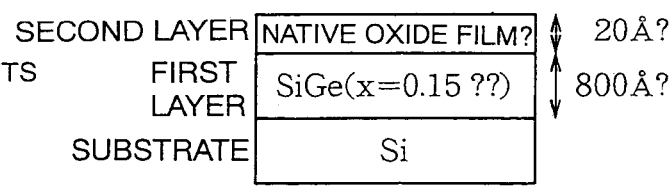
FIG. 12 is a diagram for describing the data of a model which is set in Step 21 of the composition determining method.

In Step 21, modeling is performed for a material which is to be measured with spectroscopic ellipsometer. FIG. 12 is a diagram for describing data of a model built in Step 21. The model is built, taking into consideration the manufacturing process or the like for the sample which is to be measured of which the measured data has been converted into the comparative data in the previous Step 20. Setting is made for the optical constants, composition, and film thickness (d), of the substrate and each layer.

In the present embodiment, let us make an assumption that a first layer SiGe (x=0.15), which is a compound semiconductor layer, is formed with the film thickness d of 800 Å on a Si substrate. Furthermore, let us make an assumption that a second layer which is a native oxide layer of the compound semiconductor layer is formed thereupon. Making an assumption that the second layer is formed with the film thickness d of 20 Å, the optical constants (n and k, or $\epsilon_r$ and $\epsilon_i$) and the composition ratios of the substrate and the first and second layers are setup. Note that reference data is used for the optical constants. If necessary, the reference data can be modified, using previously accumulated data and stored in database.

(Step 22)

Figure 13:
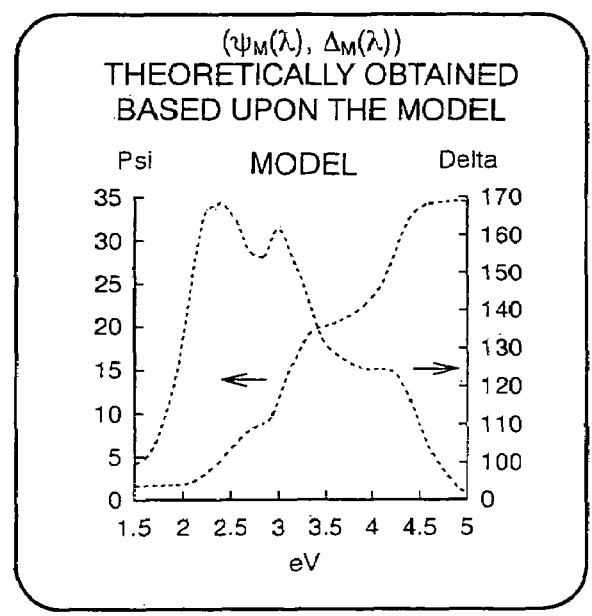
FIG. 13 is a chart which shows the data based upon the model obtained in Step 22 of the composition determining method.

In Step 22, modeling spectra are formed as a comparative data based upon the simulation model formed in the above-described Step 21. FIG. 13 is a chart which shows the data from the model calculated in Step 22. The vertical axis and the horizontal axis are the same as described in FIG. 11. The modeling spectra are formed based upon the model employed in Step 21. Setting the optical constants n and k, or $\epsilon_r$ and $\epsilon_i$ to the known values for each wavelength, and setting the aforementioned film thicknesses of the first and second layer d to the determined values, $\Psi_M(\lambda_i)$ and $\Delta_M(\lambda_i)$ are calculated, whereby the modeling spectra are formed.

(Step 23)

Figure 14:
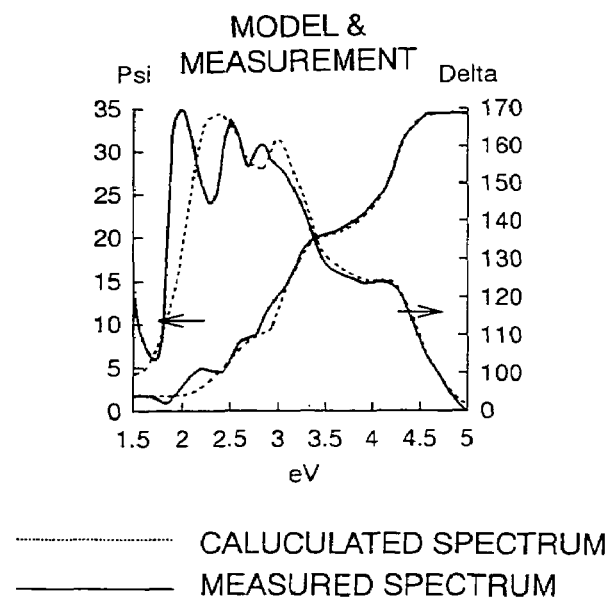
FIG. 14 is a chart wherein measured spectroscopic data which is to be compared in Step 23 of the composition determining method and the data obtained based upon the model are superimposed.

In Step 23, a comparison is made between the measured spectroscopic data and the modeling comparative data. FIG. 14 is a chart wherein the measured spectroscopic data and the modeling data, which are to be compared in Step 23, are superimposed. That is to say, the modeling spectra $\Psi_M(\lambda_i)$ and $\Delta_M(\lambda_i)$ calculated in Step 22 and the measured spectrum $\Psi_E(\lambda_i)$ and $\Delta_E(\lambda_i)$ obtained in Step 20 are compared.

(Step 24)

In Step 24, evaluation is made for the above-described comparison results. FIG. 15 is a diagram for describing fitting performed in Step 24. In this step, determination is made whether or not the measured data matches the model based upon the results of fitting parameters wherein parameters are adjusted so that the difference becomes minimal between ($\Psi_E(\lambda_i)$, $\Delta_E(\lambda_i)$) and ($\Psi_M(\lambda_i)$, $\Delta_M(\lambda_i)$) using the least square method.

Evaluation is made as follows. First, determination is made whether or not the aforementioned mean square error ($\chi^2$) of the model is within a predetermined range, or determination is made which $\chi^2$ of models obtained in Step 24 in finite repeated looping including Step 25 (Step 22→Step 23→Step 24→Step 25→Step 22) described later is minimal. Subsequently, the model corresponding to the determination is selected as the best model which matches the measured data.

(Step 25)

FIG. 16 is a diagram for describing alternation of the model in Step 25. In Step 25, in the event that determination has been made that the model does not match the measured spectroscopic data in Step 24, the model is modified to be evaluated as a new model. In this example, the film thickness of the SiGe, which is the first layer set in Step 21, is changed from 800 Å to 2000 Å, and the composition ratio x thereof is changed from 0.15 to 0.2. Furthermore, the optical constants, compositions, or the like, of each layer are changed as appropriate, whereby the next model is determined.

(Step 22)

In Step 22, the next $\Psi_M(\lambda_i)$ and $\Delta_M(\lambda_i)$ are theoretically obtained based upon the model set in Step 25. The processing of Step 23, Step 24, Step 25, and Step 22, is repeatedly performed.

(Step 26)

FIG. 17 is a diagram which shows a chart of $\Psi_M(\lambda_i)$ and $\Delta_M(\lambda_i)$ calculated from the fitted parameters (with result thickness and dispersion formula parameters) and a structure with regard to the determined model for describing Step 26. In Step 26, the data of the model determined to match the measured data in the above-described Step 24 is determined as the measurement results, and represents the end of measurement. In this example, the model is selected wherein the first layer is formed of SiGe (x=0.18) with the film thickness of 1808.4 Å and with optical constants ($n_1$, $k_1$), and the second layer is formed of native oxide of the compound semiconductor layer, with the film thickness of 20.8 Å and the optical constants ($n_2$, $k_2$), from the models evaluated in the above-described repeated processing, having exhibited the minimal $\chi^2$.

Two methods are known for determining the aforementioned composition ratio. While in the present embodiment, description has been made regarding the method for determining the composition ratio in the same time as with the film thickness and the optical constants as shown in Step 26, a method may be employed wherein the film thickness and the optical constants are obtained from the measurement results, following which the composition is determined based upon the relation between the dielectric constant (optical constant) and the composition ratio. Note that, the optical constants can be represented by the reference data, as well as the optical constants can be calculated using the dispersion formula (which represents the wavelength-dependency of the dielectric constant of the material).

Next, description will be made regarding a case that measurement is made taking the incident angle around the nominal incident angle $\phi_0$ as a parameter. As described above, the change in polarization ($\rho$) is represented by $\rho$=tan $\Psi\cdot\exp(i\Delta)$, and is dependent upon the parameters such as the wavelength ($\lambda$), the incident angle ($\phi$), the film thickness, the complex refractive index, and the like, and the relationship between these parameters can be represented by the following expression.

$$(d, n, k, \text{composition ratio})=F(\Psi, \Delta, \lambda, \phi)$$

It is anticipated that a model with the incident angle $\phi_0$ minutely modified matches the measured data better than with the model with the nominal incident angle $\phi_0$, due to minute roughness of the sample surface. Accordingly, it is reasonable to think that the above-described $\Psi_E(\lambda_i)$ and $\Delta_E(\lambda_i)$ have been measured with the incident angle modified from $\phi_0$.

That is to say, with the thin film measurement method using the aforementioned spectroscopic ellipsometer, measurement is made as follows. First, the above-described $\Psi_E(\lambda_i)$ and $\Delta_E(\lambda_i)$ are obtained by the measurement with the nominal incident angle $\phi_0$. In the above-described model simulation spectrum calculation step for obtaining the above-described $\Psi_M(\lambda_i)$ and $\Delta_M(\lambda_i)$, the simulation spectra $\Psi_{M0}(\lambda_i)$ and $\Delta_{M0}(\lambda_i)$ with the incident angle as the nominal incident angle $\phi_0$, and the simulation spectra $\Psi_{Mk}(\lambda_i)$ and $\Delta_{Mk}(\lambda_i)$ with the incident angle $\phi_k$ around the nominal incident angle $\phi_0$ are obtained. The obtained simulation spectra calculated in Step 21 are compared to $\Psi_E(\lambda_i)$ and $\Delta_E(\lambda_i)$.

Figures 18, 19:
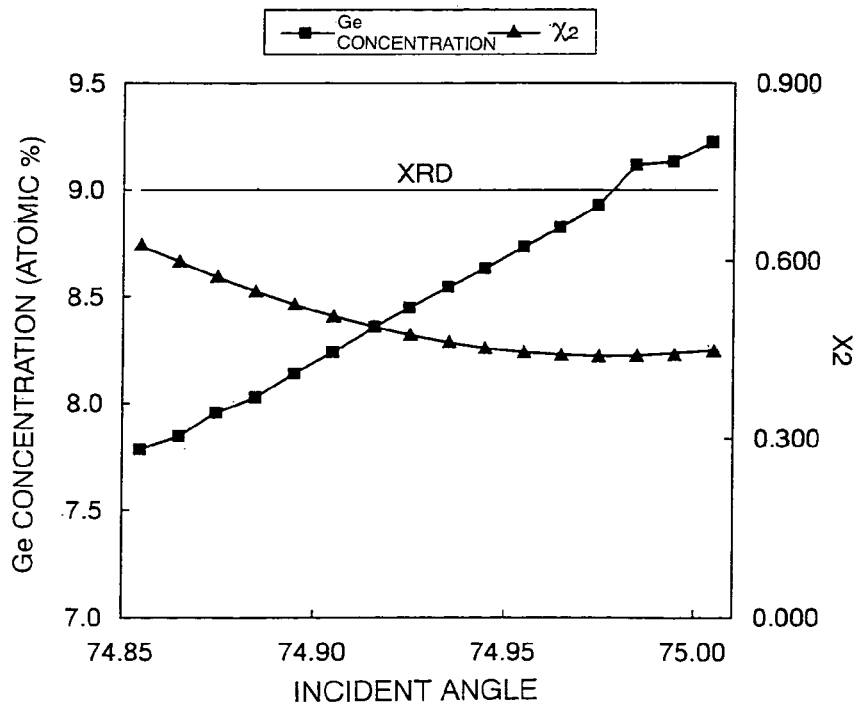
FIG. 18 is a data table used for determining the best model including the film thickness and composition ratio by performing fitting with an incident angle as a parameter in the composition determining method.
FIG. 19 is a chart which shows the data obtained by the aforementioned fitting in the composition determining method.

Now, an example will be described with reference to FIGS. 18 and 19. In FIG. 18, $\chi^2$ values are shown with the incident angles around the aforementioned nominal incident angle $\phi_0$ from $\phi_{kmin}$ of 74.85°, progressively incremented by $\Delta\phi_k$ of 0.01°. As described above, the best combination of the film thickness and the composition ratio is determined based upon the $\chi^2$ values. In this example, $\phi_{kmax}$ is set to 75.00°. In this example, the models are consecutively formed with the incident angle $\phi_k$, the film thickness d, and the composition ratio x, and fitting is performed in a step corresponding to the aforementioned Step 21 using the models. In FIG. 18, the uppermost row of the table shows the $\chi^2$ value of 0.6292 obtained from the best combination of the film thickness $d_{kmin}$ of 1100.4 Å and the composition ratio $x_{kmin}$ of 7.7876 atomic % for the incident angle $\phi_{kmin}$ of 74.85°. FIG. 19 is a chart which shows the Ge concentration in atomic % and $\chi^2$, calculated for each incident angle.

As can be understood from FIG. 18, the $\chi^2$ value obtained from the combination of the film thickness $d_{kbest}$ of 1100.3 Å and the composition ratio $x_{kbest}$ of 8.9277 atomic % for the incident angle $\phi_{kbest}$ of 74.970 exhibits the minimal value of 0.4406, and accordingly the aforementioned model is determined as the best model, whereby the best film thickness and the composition ratio are determined.

Note that the line XRD (x-ray diffraction) shown in FIG. 19 indicates the measurement results measured by a different type of a measuring technique for comparison. The concentration of Ge measured by XRD exhibits x=9.00 atomic % generally the same value as achieved with the present invention. These results show that more precise measurement values can be obtained with the method according to the present invention by performing fitting taking the incident angle as a parameter.

As described above in detail, with the composition determining method for compound semiconductor layer on a substrate according to the present invention, the composition of the thin film which has been difficult to measure can be measured more precisely and in a more sure manner by using various models, and furthermore by performing fitting of the incident angle.

(Description Regarding a Composition Determining Method for Polycrystalline Compound Semiconductor)

Figure 20:
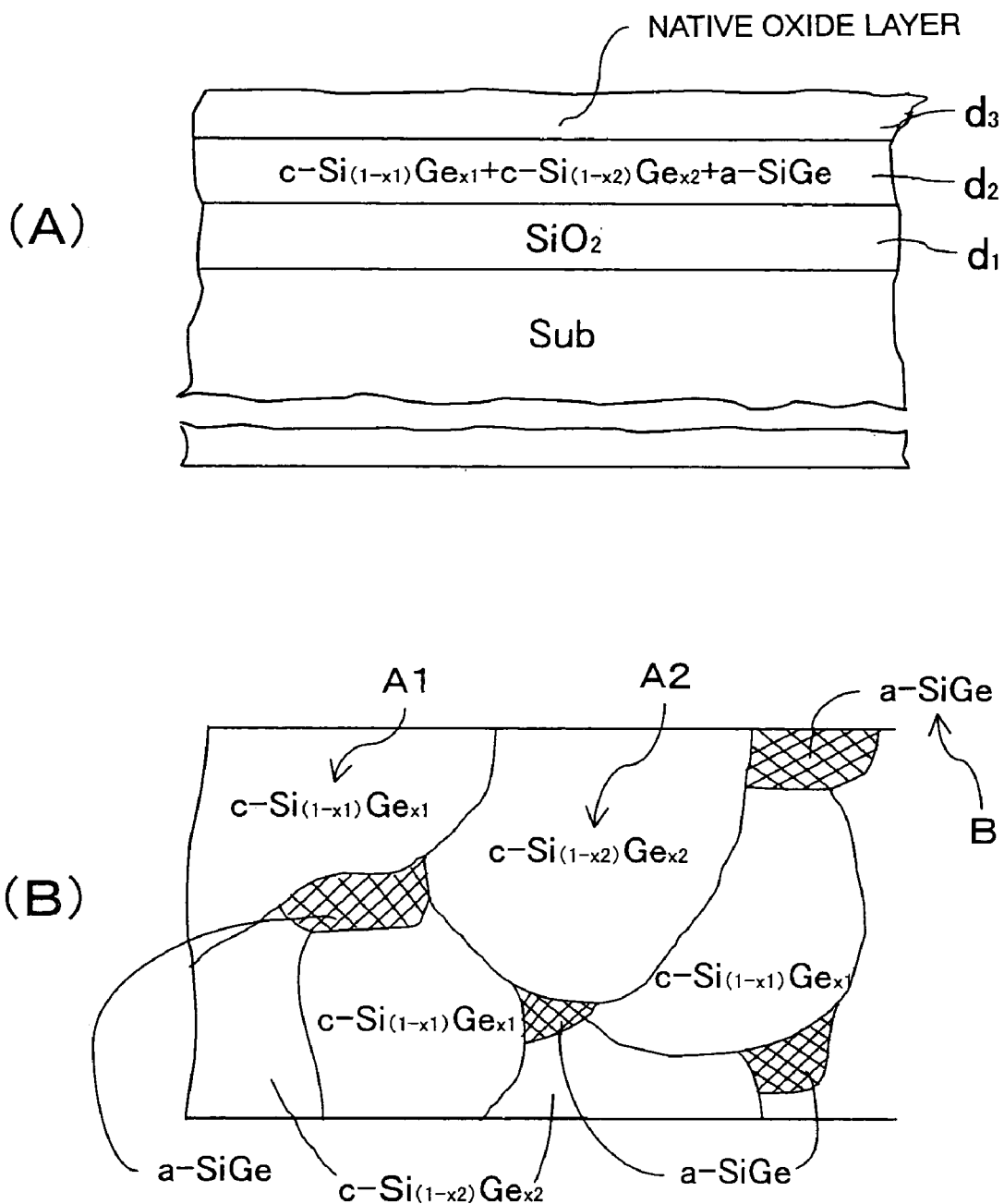
FIG. 20 is a conceptual schematic diagram which illustrates the structure of a layer which is to be measured in the composition determining method.
Figure 21:
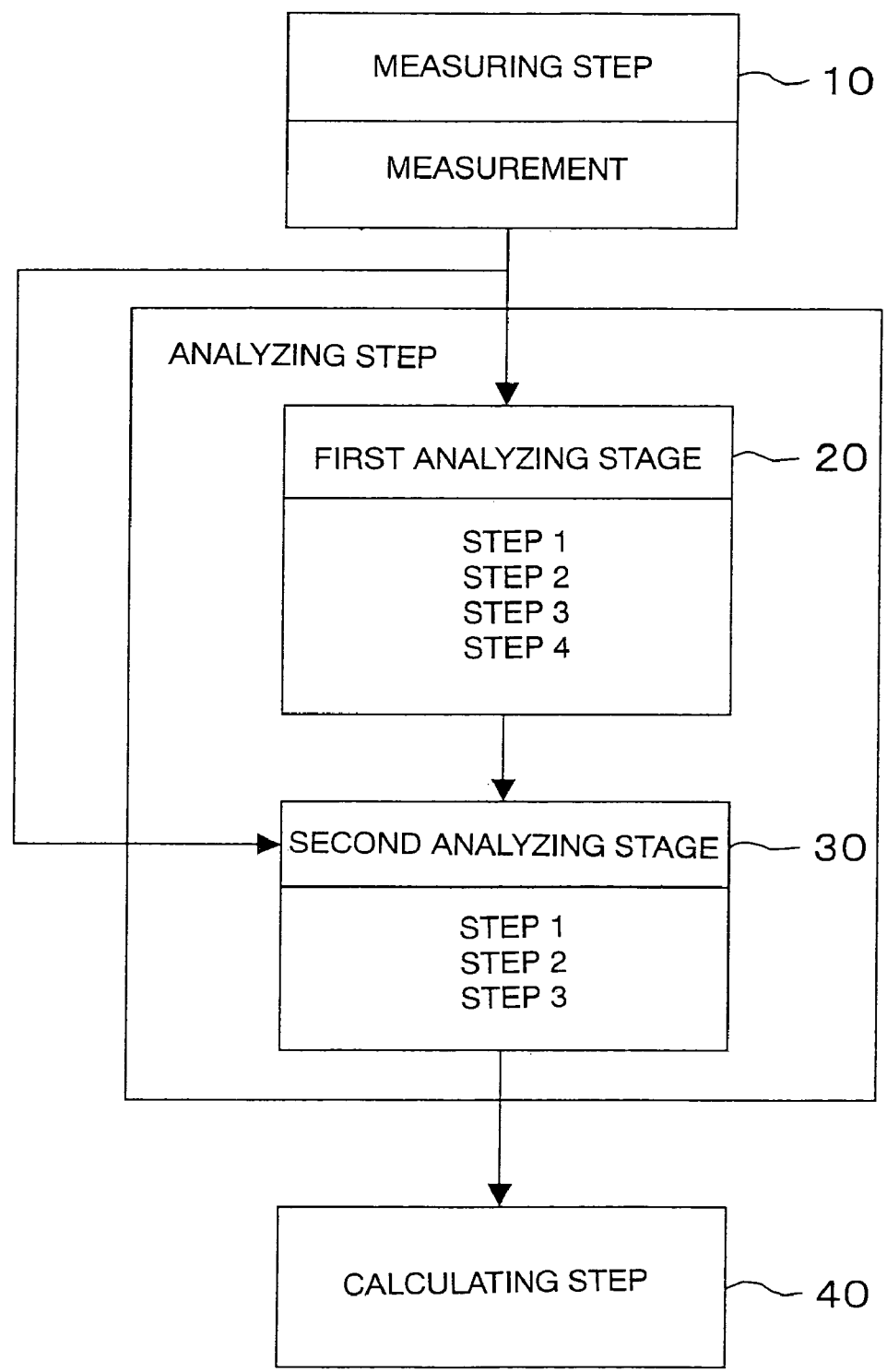
FIG. 21 is a basic flowchart which shows a composition determining method for polycrystalline compound semiconductor according to the present invention.
Figure 22:
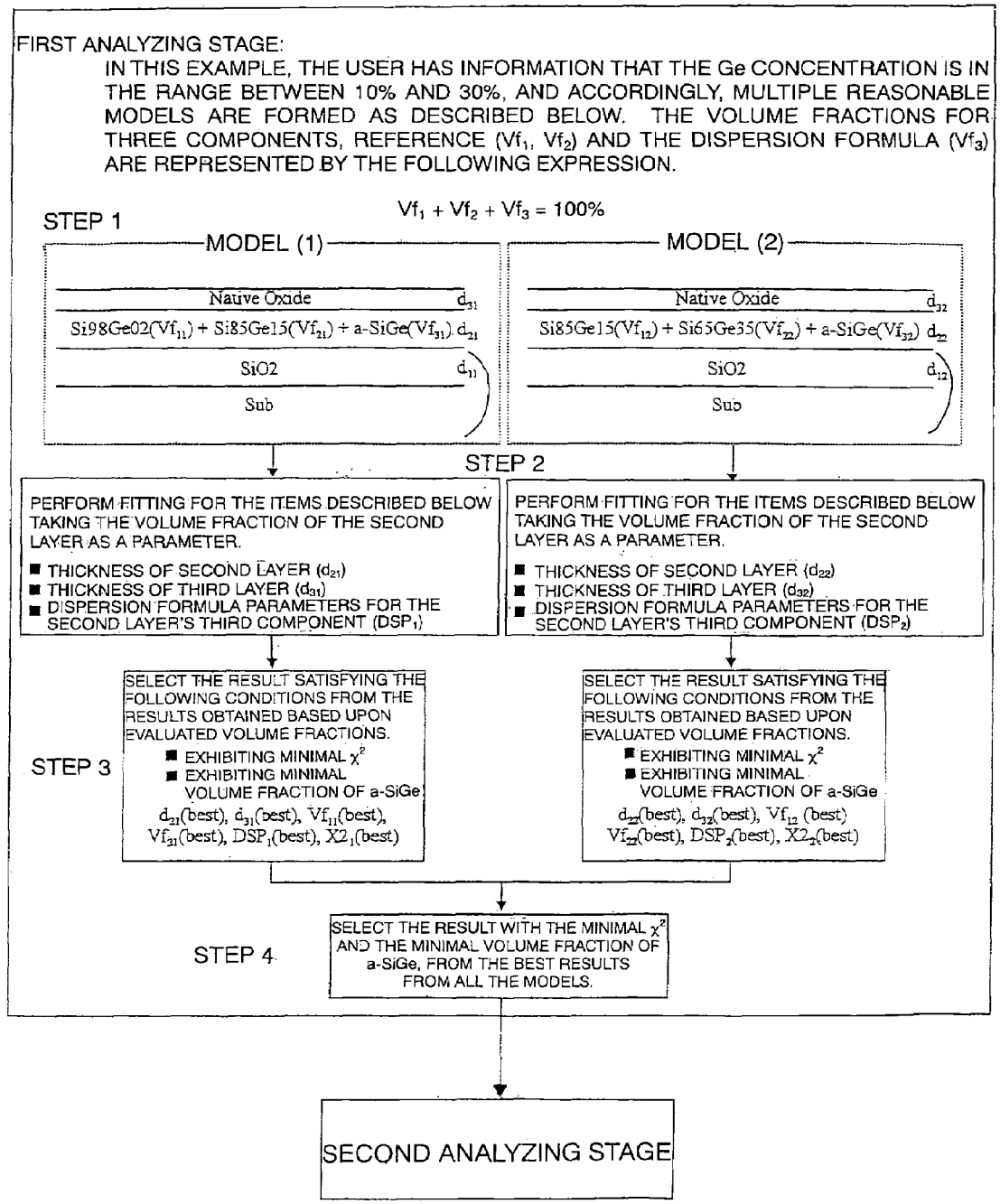
FIG. 22 is a flowchart which shows a first analyzing stage of the composition determining method, in detail.
Figure 23:
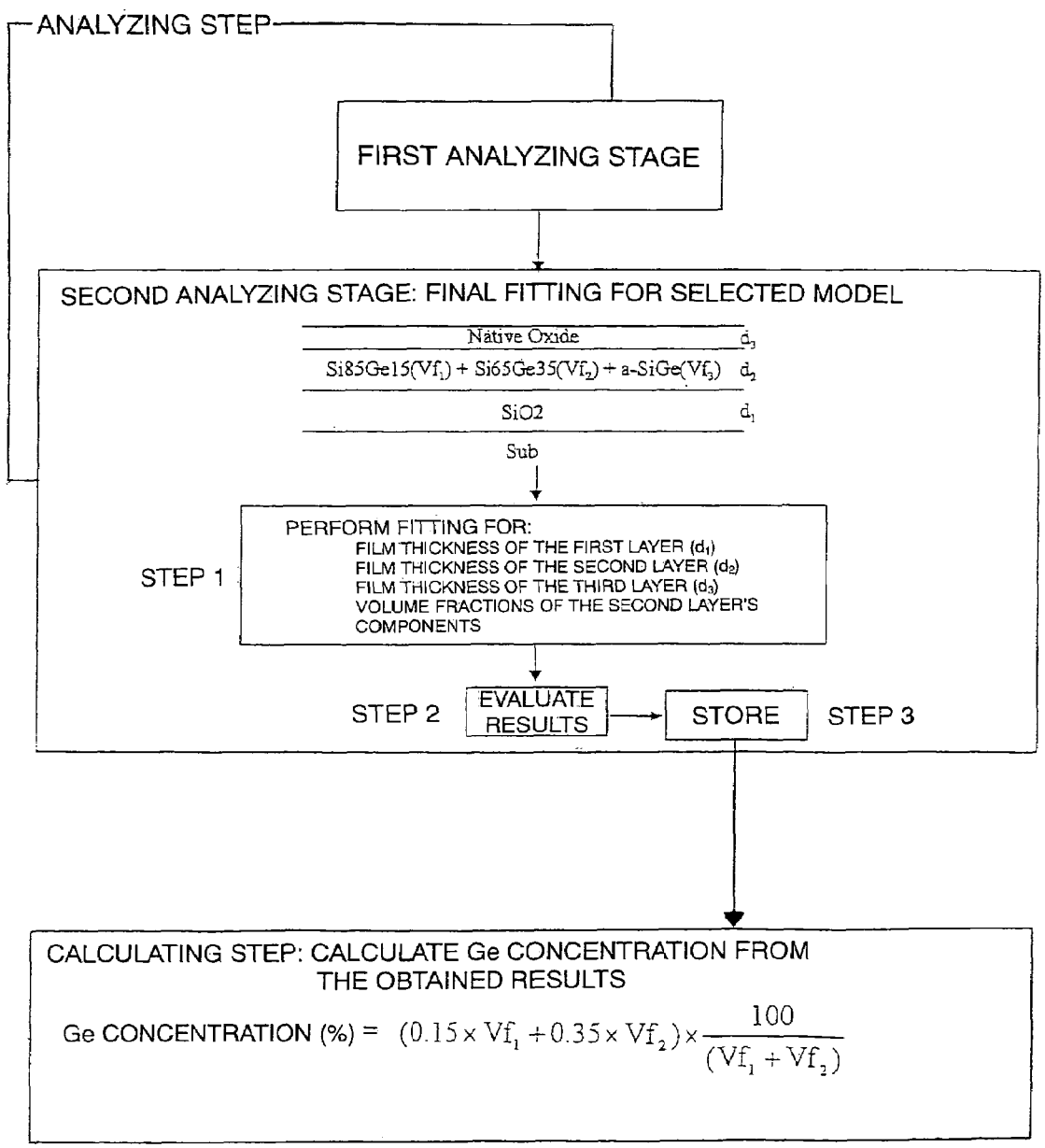
FIG. 23 is a flowchart which shows a second analyzing stage and a calculating step of the composition determining method, in detail.

Now, description will be made regarding polycrystalline SiGe as an example. FIG. 20 is a schematic diagram for describing the structure of the measuring object. FIG. 21 is a flowchart of a method according to the present invention. FIGS. 22 and 23 show a first and second analyzing stages for concentration calculation, respectively.

Now, the flow of the method according to the present invention will be described with reference to FIG. 21. First, measurement is made with the apparatus shown in FIG. 1. The measurement process includes a spectrum measurement step 10 for obtaining $\Psi_E(\lambda_i)$ and $\Delta_E(\lambda_i)$ for each wavelength $\lambda_i$ in a predetermined range, which represent the change in polarization of incident light and the reflected light, an analyzing step 20 including a first analyzing stage 20 and a second analyzing stage 30, and a calculating step 40 for calculating the concentration of Ge based upon the analyzed results.

[Measurement Step]

Now, description will be made in brief regarding the spectroscopic ellipsometer used in the measuring step.

A Xe lamp 1 is a so-called white light source for emitting light containing a great number of wavelength components. The light emitted from the Xe lamp 1 is introduced to a polarizer 3 through an optical fiber 2. The light polarized by the polarizer 3 is cast onto the surface of a sample 4 which is to be measured with a predetermined incident angle (e.g., $\phi=75.00°$).

The reflected light from the sample 4 is introduced to an analyzer 6 through a photo-elastic modulator (PEM) 5. The reflected light is subjected to phase modulation with a frequency of 50 kHz by the photo-elastic modulator (PEM) 5. As a result the polarization of the reflected light, which is originated from the linearly polarized incident light, will change periodically from linearly to elliptically. Accordingly, $\Psi$ and $\Delta$ can be determined within several msec. The output from the analyzer 6 is connected to a spectroscope 8 through an optical fiber 7. The output data from the spectroscope 8 is acquired by a data acquisition unit 9, whereby the spectroscopic measurement step 10 to obtain the measured spectroscopic data ends. Note that the PEM 5 may be situated in front of the polarizer 3 or the analyzer 6.

[First Analyzing Stage]

Let us say that a layer which is to be measured in this example includes a first material (a1), a second material (a2), and a third material (b), which have different optical constants. Furthermore, let us say that these materials have been mixed with the volume fraction of $Vf_1: Vf_2: Vf_3$ ($Vf_1+Vf_2+Vf_3=100\%$).

Detailed composition will be shown below.

a1: c-SiGe with composition of $Si_{(1-x1)}Ge_{x1}$ and with volume fraction of $Vf_1$ a2: c-SiGe with composition of $Si_{(1-x2)}Ge_{x2}$ and with volume fraction of $Vf_2$ b: a-SiGe, i.e., amorphous SiGe with volume fraction of $Vf_3$ (Step 1)

Let us say that we have information that the sample which is to be measured in this example contains Ge at a concentration of 10 atomic % to 30 atomic %. Models (1) and (2) are built taking this information into consideration. Note that $Si_{98}Ge_{02}$, $Si_{85}Ge_{15}$, and $Si_{65}Ge_{35}$ denote reference names, and indicate the composition ratio x of 0.02, 0.15, and 0.35, respectively.

Model (1)

| | | |
|---|---|---|
| Third layer: | native oxide layer | $d_{31}$ |
| Second layer: | $Si_{98}Ge_{02}(Vf_{11}) + Si_{85}Ge_{15}(Vf_{21}) + a\text{-}SiGe(Vf_{31})$ | $d_{21}$ |
| First layer: | $SiO_2$ | $d_{11}$ |
| Substrate: | Si | bulk |

Model (2)

| | | |
|---|---|---|
| Third layer: | native oxide layer | $d_{32}$ |
| Second layer: | $Si_{85}Ge_{15}(Vf_{12}) + Si_{65}Ge_{35}(Vf_{22}) + a\text{-}SiGe(Vf_{32})$ | $d_{22}$ |
| First layer: | $SiO_2$ | $d_{12}$ |
| Substrate: | Si | bulk |

(Step 2) See FIG. 22

In the above-described models (1) and (2), reference data can be used for the first and third layers. On the other hand, with the second layers in the models (1) and (2), the composition ratios of the first and second materials a1 of c-SiGe ($Si_{(1-x1)}Ge_{x1}$) and a2 formed of c-SiGe ($Si_{(1-x2)}Ge_{x2}$) are known, and reference data thereof can be used, but reference data can not be used for the third material b1 of a-SiGe. Accordingly, fitting is made as described below, using the volume fractions (Vf) of the second layer as parameters.

First, with regard to the model (1), fitting is made as described below, using the volume fractions (Vf) of the second layer as parameters.

Film thickness of the second layer ($d_{21}$)

Film thickness of the third layer ($d_{31}$)

Dispersion formula parameters for the second layer of a-SiGe ($DSP_1$)

Next, with regard to the model (2), fitting is made as described below, using the volume fractions (Vf) of the second layer as parameters.

Film thickness of the second layer ($d_{22}$)

Film thickness of the third layer ($d_{32}$)

Dispersion formula parameters for the second layer of a-SiGe ($DSP_2$)

(Step 3) See FIG. 22

With regard to the model (1), the results matching the following conditions are selected from the fitting results based upon the volume fractions used as parameters.

Condition 1: Calculated $\chi^2$ is the minimal

Condition 2: The volume fraction of a-SiGe is the minimal

Determined best values: $d_{21(best)}$, $d_{31(best)}$, $Vf_{11(best)}$, $Vf_{21(best)}$, $DSP_{1(best)}$, and $\chi^2_{1(best)}$ With regard to the model (2), the results matching the following conditions are selected from the fitting results based upon the volume fractions used as parameters.

Condition 1: Calculated $\chi^2$ is the minimal

Condition 2: The volume fraction of a-SiGe is the minimal

Determined best values: $d_{22(best)}$, $d_{32(best)}$, $Vf_{12(best)}$, $Vf_{22(best)}$, $DSP_{2(best)}$, and $\chi^2_{2(best)}$ In this example, an assumption is made that the p-SiGe layer is formed of the mixture of the c-SiGe with a known composition ratio and the a-SiGe with an unknown composition ratio. That is to say, the composition of the c-SiGe is known value, but the precise composition of the a-SiGe is unknown. Accordingly, the smaller the composition ratio of the a-SiGe is, the more precise Ge concentration of the p-SiGe can be calculated based upon the reference data of c-SiGe. Accordingly, description has been made regarding a case of selecting the results with the minimal volume fraction of a-SiGe.

(Step 4) See FIG. 22

Furthermore, the best model and results are selected from the best results for all the models with the conditions that $\chi^2$ and the volume fraction of the a-SiGe are the minimal.

[Second Analyzing Stage]

In the second analyzing stage, the final fitting is made with regard to the best model selected in the previous step.

Third layer ($d_3$): Native oxide layer

Second layer ($d_2$): $Si_{85}Ge_{15}(Vf_1)+Si_{65}Ge_{35}(Vf_2)$+a-SiGe ($Vf_3$)

First layer ($d_1$): $SiO_2$

Substrate: Si (Step 1)

Fitting is made with regard to the above-described best model, taking the following values as parameters.

[Parameters]

Film thickness ($d_1$) of the first layer

Film thickness ($d_2$) of the second layer

Film thickness ($d_3$) of the third layer

Volume fractions (Vf) of the materials contained in the second layer (Step 2)

The fitting results of the previous step are evaluated.

(Step 3)

The evaluated results are stored.

[Calculating Step]

As an example, let us say that the composition ratios and the volume fractions of the materials contained in the second layer are determined in the above-described analyzing step as follows. In this case, the Ge concentration is calculated with the following algorithm in the calculating step. Note that $Si_{85}Ge_{15}$ and $Si_{65}Ge_{35}$ are the reference names, and denote the concentrations x of 0.15 and 0.35, respectively, in this example.

In this example, $Si_{(1-x1)}Ge_{x1}(Vf_1)$, $Si_{(1-x2)}Ge_{x2}(Vf_2)$, and a-SiGe($Vf_3$) are $Si_{85}Ge_{15}$(72.2%), $Si_{65}Ge_{35}$(9.23%), and a-SiGe(18.57%), in reality. These values are applied to the following expression.

Ge concentration (atomic %)=$(X1 \cdot Vf_1+X2 \cdot Vf_2) \cdot 100/(Vf_1+Vf_2)$=(0.15×72.2+0.35×9.23)×100/(72.2+9.23)=17.27 [atomic %]

As described in detail, with the composition determining method for polycrystalline compound semiconductor using a spectroscopic ellipsometer according to the present invention, the Ge concentration of polycrystalline SiGe formed on a substrate can be obtained based upon the data obtained using the spectroscopic ellipsometer with the new approximate calculation.

According to the present invention:

1. The Ge concentration of polycrystalline SiGe can be calculated quickly and in a simple manner, even without precise reference data for the polycrystalline SiGe for each crystallization ratio and each Ge concentration.

2. As described above, with the method according to the present invention, not only the composition of polycrystalline SiGe can be determined, but also the compositions of various polycrystalline materials can be generally determined.

3. The smaller the volume fraction of the amorphous component is, the better the precision of this method is. It can be stated from experience that the concentration of the atom of interest can be obtained with satisfactory precision, even in the event that the volume fraction of the amorphous component is around 20%.

Various modifications can be made within the scope of the present invention. To facilitate understanding, description has been made regarding acquisition of data and setting of models, using $\Psi$ and $\Delta$, throughout the present specification. Furthermore, the measurement and fitting can be performed in the same way for data set of (n, k), ($\epsilon_i$, $\epsilon_r$), (tan $\Psi$, cos $\Delta$), or ($I_s$, $I_c$), well known by one skilled in the art, and are encompassed in the present invention.

While description has been made regarding an example wherein a single layer of $SiO_2$ has been formed on a substrate, the present invention can be applied to measurement for single-layer structures or multi-layer structures formed of various materials, and measurement of film thickness in a wide range, as well. Furthermore, while description has been made regarding an example wherein Si substrate is employed, the present invention can be applied to arrangements wherein substrates of other materials (e.g., transparent substrates formed of other materials such as glass, quartz, or the like, or substrates formed of compound semiconductors) are employed, as well.

Furthermore, while detailed description has been made regarding a case of SiGe as an example of the aforementioned compound semiconductor, the present invention can be applied to determination of the composition of other compound semiconductor layers such as AlGaAs, InGaAsP, InGaAs, InAlAs, InGaP, AlGaInP, AlGaInAs, AlGaAsSb, InAsSb, HgCdTe, ZnMgSSe, ZnSSe, ZnCdSe, ZnMnSe, ZnFeSe, and ZnCoSe, as well. Furthermore, while description has been made regarding an arrangement wherein a single layer of SiGe has been formed on a substrate, the present invention can be applied to measurement of multi-layer structures formed of other materials, or to measurement of film thickness in a wide range. Furthermore, while description has been made regarding an example that Si substrate is employed, the present invention can be applied to arrangements wherein substrates of other materials (e.g., transparent substrates formed of other materials such as glass, quartz, or the like, or substrate formed of compound semiconductor) are employed, as well.

While description has been made regarding a composition determining method for compound semiconductor, wherein the composition ratios are obtained at the same time as with the film thickness and optical constants as shown in Step 26, a method can be employed wherein the film thickness and the optical constants are obtained from the measured results, following which the composition ratios are determined based upon the relation between the dielectric constant (optical constant) and the composition ratios, which is also encompassed in the technical scope of the present invention.

While description has been made regarding an arrangement wherein known values (reference data) are employed for the optical constants, an arrangement may be made wherein the optical constants are calculated based upon the dispersion formula or the like which represents the wavelength dependency of the dielectric constant of the material, which is encompassed in the technical scope of the present invention. Furthermore, in a case of using a dispersion formula, an arrangement may be made wherein known values are employed for optical constants, which is encompassed in the technical scope of the present invention.

While description has been made regarding an arrangement wherein a layer of $SiO_2$ and a layer of SiGe are formed on a substrate, the present invention can be applied not only to the structure formed of the materials, but also to applications in a wide range, i.e., various structures formed of various materials with various film thicknesses. Furthermore, while description has been made regarding an arrangement wherein measurement is made using an ellipsometer with the PEM, an arrangement may be made wherein measurement is made using an ellipsometer without the PEM.

Furthermore, the present invention can be similarly applied to an arrangement wherein a substrate other than Si substrate, such as a transparent substrate formed of glass, quartz, or the like, a compound semiconductor substrate, or the like, is employed. Furthermore, the present invention is not restricted to any particular kind of substrate, but rather the present invention can be applied to a substrate with any surface state, i.e., the present invention can be applied to both smooth and rough substrates.

The dispersion formulas used for the present invention include not only the formula based upon classical mechanics or quantum mechanics and empirical formulas, but also various other formulas including other parameters, which are encompassed in the technical scope of the present invention.

While description has been made regarding an arrangement wherein all the parameters are determined at the same time by fitting, an arrangement may be made wherein a part of the parameters are determined in the following step, which is also encompassed in the technical scope of the present invention.

While description has been made regarding an arrangement wherein measurement is made using the EMA, an arrangement may be made wherein other effective medium theory is employed, which is also encompassed in the technical scope of the present invention.

While description has been made regarding a measuring method for a polycrystalline compound semiconductor layer containing the mixture of the crystalline compound semiconductors both containing the atom of interest and the amorphous compound semiconductor containing the atom of interest, the present invention can be applied to a method for a polycrystalline compound semiconductor layer which contains the crystalline compound semiconductor not containing the atom of interest, which is also encompassed in the technical scope of the present invention.

While description has been made regarding a method for determining the composition of a single layer, the present invention can be applied to a method for determining the compositions of two or more layers, which is also encompassed in the technical scope of the present invention.

While description has been made regarding a method for determining the composition of a layer formed of the mixture of two kinds of crystalline compound semiconductor and one kind of amorphous compound semiconductor, the present invention can be applied to a method for determining the composition of a layer formed of the mixture of one or three or more kinds of crystalline compound semiconductor and one kind of amorphous compound semiconductor, which is also encompassed in the technical scope of the present invention.

Part or all of the above described methods can be performed automatically (by a computer, robot, or the like) or manually, which is also encompassed in the technical scope of the present invention.

Description has been made regarding an arrangement wherein measurement is made with an incident angle of 75°, but an arrangement may be made wherein measurement is made with an incident angle other than the aforementioned angle, which is also included in the technical scope of the present invention.

While description has been made regarding a method for analyzing by taking an incident angle around the nominal incident angle (750) as a parameter, an arrangement may be made wherein analysis is made taking an incident angle around the measured incident angle as a parameter, which is also encompassed in the technical scope of the present invention.

Furthermore, an arrangement may be made wherein measurement is made with multiple incident angles automatically (Variable Angle Measurement), and analysis is made based upon all of the measured data, or based upon the data with regard to a specified angle of the aforementioned multiple incident angles, which is also encompassed in the technical scope of the present invention. Furthermore, an arrangement may be made wherein fitting is performed for all of the measured data, or for the data with regard to the specified incident angle, taking an incident angle around each measuring incident angle as a parameter, which is encompassed in the technical scope of the present invention.

What is claimed is:

1. A composition determining method for a compound semiconductor layer wherein the surface of a compound semiconductor layer formed on a substrate is measured using a spectroscopic ellipsometer, and the composition ratios x and y of said compound semiconductor layer formed on said substrate are determined, said composition determining method comprising:

a spectrum measuring step for obtaining spectra $\Psi_E(\lambda_i)$ and $\Delta_E(\lambda_i)$ by measuring a thin film on a substrate which is to be measured with various wavelengths of incident light, which represent the change in polarization of said incident light and the reflected light for each wavelength $\lambda_i$;

a modeling spectrum calculating step wherein a model including said substrate with ($N_0(n_0, k_0)$), and j-th layers with ($d_j$, $N_j(n_j, k_j)$), is formed, and modeling spectra $\Psi_M(\lambda_i)$ and $\Delta_M(\lambda_i)$ are obtained based upon said model;

a comparative evaluating step wherein comparison is made between said measured spectra $\Psi_E(\lambda_i)$ and $\Delta_E(\lambda_i)$ and said modeling spectra $\Psi_M(\lambda_i)$, and $\Delta_M(\lambda_i)$, and the structure corresponding to said modeling spectra $\Psi_M(\lambda_i)$ and $\Delta_M(\lambda_i)$ satisfying predetermined evaluation criteria is determined as the measured result (d, n, k, and the composition ratio are determined); and a modifying step wherein said model not satisfying said predetermined evaluation criteria is modified, and processing in said modeling spectrum calculating step and processing in said comparative evaluating step are performed again.

2. A composition determining method for a compound semiconductor layer on a substrate according to claim 1, wherein evaluation of said model is performed with an evaluation criterion wherein mean square error of said measured spectra $\Psi_E(\lambda_i)$ and $\Delta_E(\lambda_i)$ and said modeling spectra $\Psi_M(\lambda_i)$ and $\Delta_M(\lambda_i)$ is obtained for each model, and the model with the minimal mean square error is determined to be the best model.

3. A composition determining method for a compound semiconductor layer on a substrate according to claim 1, wherein simulation spectra $\Psi_{Mk}(\lambda_i)$ and $\Delta_{Mk}(\lambda_i)$ are calculated with an incident angle $\phi_k$ as a parameter around said nominal incident angle $\phi_0$ used in said spectrum measuring step, in said model simulation spectrum calculating step;

and wherein a comparison is made between said measured spectra $\Psi_E(\lambda_i)$ and $\Delta_E(\lambda_i)$ and said modeling spectra $\Psi_{Mk}(\lambda_i)$ and $\Delta_{Mk}(\lambda_i)$, and the structure corresponding to said modeling spectra $\Psi_{Mk}(\lambda_i)$ and $\Delta_{Mk}(\lambda_i)$ satisfying predetermined evaluation criteria is determined as the measured result in said comparative evaluating step.

4. A composition determining method for a compound semiconductor layer on a substrate according to claim 1, wherein said composition determining processing is performed for a compound semiconductor layer formed of SiGe, AlGaAs, InGaAsP, InGaAs, InAlAs, InGaP, AlGaInP, AlGaInAs, AlGaAsSb, InAsSb, HgCdTe, ZnMgSSe, ZnSSe, ZnCdSe, ZnMnSe, ZnFeSe, or ZnCoSe.

5. A composition determining method for polycrystalline compound semiconductor using a spectroscopic ellipsometer, comprising:
a spectrum measuring step for obtaining spectra $\Psi_E(\lambda_i)$ and $\Delta_E(\lambda_i)$ by measuring said polycrystalline compound semiconductor layer with various wavelengths of incident light, which represent the change in polarization of said incident light and the reflected light for each wavelength $\lambda_i$; and
a first analyzing stage including:
a first step for forming a plurality of models including said substrate with the complex refractive index of $(N_0(n_0, k_0))$ and layers with the complex refractive indexes of $(N_1(n_1, k_1))$, $(N_2(n_2, k_2))$, and so on, and with film thicknesses, wherein the complex refractive index of said polycrystalline compound semiconductor layer is calculated based upon an assumption that said polycrystalline compound semiconductor layer is formed of the mixture of crystalline compound semiconductor containing an atom of interest, and amorphous compound semiconductor containing said atom of interest,
a second step for obtaining parameters of a dispersion formula for said unknown amorphous compound semiconductor by performing fitting with said film thicknesses and the volume fraction as variables,
a third step for selecting the result with the minimal mean square error and the minimal volume fraction of said amorphous compound semiconductor from said fitting results, and
a fourth step for selecting the result with the minimal mean square error and the minimal volume fraction of said amorphous compound semiconductor from said best results from a plurality of models.

6. A composition determining method for polycrystalline compound semiconductor using a spectroscopic ellipsometer according to claim 5, further comprising:
a second analyzing stage including:
a first step for obtaining the film thickness and the volume fraction of said polycrystalline compound semiconductor layer or other layers by performing fitting based upon the best model obtained in said step 4 in said first analyzing stage,
a second step for evaluating said fitting results, and
a third step for storing said evaluated results; and
a calculating step for calculating the composition of the atom of interest based upon the volume fraction of said polycrystalline compound semiconductor layer and the composition ratio of said atom of interest contained in said polycrystalline compound semiconductor layer.

7. A composition determining method for polycrystalline compound semiconductor using a spectroscopic ellipsometer according to claim 5, wherein making an assumption that said polycrystalline compound semiconductor layer is formed of the mixture of a crystalline component (known reference data can be used) and an amorphous component, the composition ratio of said polycrystalline compound semiconductor is obtained based upon the composition ratio and the volume fraction of said corresponding crystalline component;
and wherein making an assumption that said polycrystalline compound semiconductor layer is formed of two kinds of crystalline compound semiconductor a1 and a2, which contain two kinds of atoms P and Q with different composition ratios (X) of the atom of interest Q, and one kind of amorphous compound semiconductor b containing said atom of interest Q, i.e., said polycrystalline compound semiconductor layer is formed of a1 formed of $P_{(1-x1)}Q_{x1}$ with the volume fraction of $Vf_1$, a2 formed of $P_{(1-x2)}Q_{x2}$ with the volume fraction of $Vf_2$, and b formed of R with the volume fraction $Vf_3$, the concentration of said atom of interest contained in said polycrystalline compound semiconductor is calculated in a concentration calculation step with the expression {Concentration of the atom of interest contained in polycrystalline compound semiconductor= $(X1 \cdot Vf_1 + X2 Vf_2) \, 100/(Vf_1 + Vf_2)$ [atomic %]}.

8. A composition determining method for polycrystalline compound semiconductor according to claim 5, wherein approximate calculation is performed making an assumption that the composition ratio of said amorphous component of said polycrystalline compound semiconductor is the same as the effective composition ratio of said crystalline component thereof.

9. A composition determining method for polycrystalline compound semiconductor using a spectroscopic ellipsometer according to claim 5, wherein said a1 represents crystalline SiGe with Ge concentration of x1 $(Si_{(1-x1)}Ge_{x1})$ and with the volume fraction of $Vf_1$, said a2 represents crystalline SiGe with Ge concentration of x2 $(Si_{(1-x2)}Ge_{x2})$ and with the volume fraction of $Vf_2$, and said b represents amorphous SiGe with the volume fraction of Vf3.

10. A composition determining method for polycrystalline compound semiconductor using a spectroscopic ellipsometer according to claim 6, further comprising:
a spectrum measuring step for obtaining spectra $\Psi_E(\lambda_i)$ and $\Delta_E(\lambda_i)$ by measuring said polycrystalline compound semiconductor layer on a substrate which is to be measured with various wavelengths of incident light, which represent the change in polarization of said incident light and the reflected light for each wavelength $\lambda_i$; and
a second step wherein processing up to said first step of said second analyzing stage described in claim 9 is performed for a plurality of measurement conditions (Zi) which can be anticipated, and the model with the minimal mean square error, or the model with the minimal mean square which is in a predetermined range between the predetermined minimal and maximal values of the film thickness, parameters of the dispersion formula, volume fraction, or incident angle, is selected from the results obtained for said plurality of measurement conditions.

11. A composition determining method for polycrystalline compound semiconductor using a spectroscopic ellipsometer according to claim 5, wherein the mean square errors of the fining results and measured values are obtained, and the minimal mean square error, or the minimal mean square error of which the corresponding value is in a predetermined range between the predetermined minimal and maximal values of the film thickness, parameters of the dispersion formula, volume fraction, or incident angle, is selected as the minimal mean square error value in steps for selecting the result with the minimal error in said first and second analyzing stages.

12. A composition determining method for polycrystalline compound semiconductor using a spectroscopic ellipsometer according to claim 5, wherein making an assumption that said polycrystalline compound semiconductor layer is formed of the mixture of a crystalline component (known reference data can be used) and an amorphous component, the composition ratio of said polycrystalline compound semiconductor is obtained based upon the composition ratio and the volume fraction of said corresponding crystalline component;

and wherein making an assumption that said polycrystalline compound semiconductor layer is formed of two kinds of crystalline compound semiconductor a1 and a2, which contain two kinds of atoms P and Q with different composition ratios (X) of the atom of interest Q, and one kind of amorphous compound semiconductor b containing said atom of interest Q, i.e., said polycrystalline compound semiconductor layer is formed of a1 formed of $P_{(1-x1)}Q_{x1}$ with the volume fraction of $Vf_1$, a2 formed of $P_{(1-x2)}Q_{x2}$ with the volume fraction of $Vf_2$, and b formed of R with the volume fraction $Vf_3$, the concentration of said atom of interest contained in said polycrystalline compound semiconductor is calculated in a concentration calculation step with the expression {Concentration of the atom of interest contained in polycrystalline compound semiconductor= $(X1Vf_1+X2Vf_2)$ $100(Vf_1+Vf_2)$ [atomic %]};

further comprising:
a second analyzing stage including:
 a first step for obtaining the film thickness and the volume fraction of said polycrystalline compound semiconductor layer or other layers by performing fitting based upon the best model obtained in said step 4 in said first analyzing stage,
 a second step for evaluating said fining results, and
 a third step for storing said evaluated results; and
a calculating step for calculating the composition of the atom of interest based upon the volume fraction of said polycrystalline compound semiconductor layer and the composition ratio of said atom of interest contained in said polycrystalline compound semiconductor layer.

13. A composition determining method for polycrystalline compound semiconductor using a spectroscopic ellipsometer according to claim 5, wherein approximate calculation is performed making an assumption that the composition ratio of said amorphous component of said polycrystalline compound semiconductor is the same as the effective composition ratio of said crystalline component thereof, further comprising:
a second analyzing stage including:
a first step for obtaining the film thickness and the volume fraction of said polycrystalline compound semiconductor layer or other layers by performing fitting based upon the best model obtained in said step 4 in said first analyzing stage,
a second step for evaluating said fitting results, and
a third step for storing said evaluated results; and
a calculating step for calculating the composition of the atom of interest based upon the volume fraction of said polycrystalline compound semiconductor layer and the composition ratio of said atom of interest contained in said polycrystalline compound semiconductor layer.

14. A composition determining method for polycrystalline compound semiconductor using a spectroscopic ellipsometer according to claim 1, wherein approximate calculation is performed making an assumption that the composition ratio of said amorphous component of said polycrystalline compound semiconductor is the same as the effective composition ratio of said crystalline component thereof
wherein making an assumption that said polycrystalline compound semiconductor layer is formed of the mixture of a crystalline component (known reference data can be used) and an amorphous component, the composition ratio of said polycrystalline compound semiconductor is obtained based upon the composition ratio and the volume fraction of said corresponding crystalline component;
and wherein making an assumption that said polycrystalline compound semiconductor layer is formed of two kinds of crystalline compound semiconductor a1 and a2, which contain two kinds of atoms P and Q with different composition ratios (X) of the atom of interest Q, and one kind of amorphous compound semiconductor b containing said atom of interest Q, i.e., said polycrystalline compound semiconductor layer is formed of a1 formed of $P_{(1-x1)}Q_{x1}$ with the volume fraction of $Vf_1$, a2 formed of $P_{(1-x2)}Q_{x2}$ with the volume fraction of $Vf_2$, and b formed of R with the volume fraction $Vf_3$, the concentration of said atom of interest contained in said polycrystalline compound semiconductor is calculated in a concentration calculation step with the expression {Concentration of the atom of interest contained in polycrystalline compound semiconductor= $(X1Vf_1+X2Vf_2)$ $100/(Vf_1Vf_2)$ [atomic %]}.

15. A composition determining method for polycrystalline compound semiconductor using a spectroscopic ellipsometer according to claim 5, wherein said a1 represents crystalline SiGe with Ge concentration of x1 ($Si_{(1-x1)}Ge_{x1}$) and with the volume fraction of $Vf_1$, said a2 represents crystalline SiGe with Ge concentration of x2 ($Si_{(1-x2)}Ge_{x2}$) and with the volume fraction of $Vf_2$, and said b represents amorphous SiGe with the volume fraction of $Vf_3$;
further comprising:
a second analyzing stage including:
a first step for obtaining the film thickness and the volume fraction of said polycrystalline compound semiconductor layer or other layers by performing fitting based upon the best model obtained in said step 4 in said first analyzing stage,
a second step for evaluating said fitting results, and
a third step for storing said evaluated results; and
a calculating step for calculating the composition of the atom of interest based upon the volume fraction of said polycrystalline compound semiconductor layer and the composition ratio of said atom of interest contained in said polycrystalline compound semiconductor layer.

16. A composition determining method for polycrystalline compound semiconductor using a spectroscopic ellipsometer according to claim 5, wherein said a1 represents crystalline SiGe with Ge concentration of x1 ($Si_{(1-x1)}Ge_{x1}$) and with the volume fraction of $Vf_1$, said $a_2$ represents crystalline SiGe with Ge concentration of x2 ($Si_{(1-x2)}Ge_{x2}$) and with the volume fraction of $Vf_2$, and said b represents amorphous SiGe with the volume fraction of $Vf_3$;

wherein making an assumption that said polycrystalline compound semiconductor layer is formed of the mixture of a crystalline component (known reference data can be used) and an amorphous component, the composition ratio of said polycrystalline compound semiconductor is obtained based upon the composition ratio and the volume fraction of said corresponding crystalline component;

and wherein making an assumption that said polycrystalline compound semiconductor layer is formed of two kinds of crystalline compound semiconductor a1 and a2, which contain two kinds of atoms P and Q with different composition ratios (X) of the atom of interest Q, and one kind of amorphous compound semiconductor b containing said atom of interest Q, i.e., said polycrystalline compound semiconductor layer is formed of a1 formed of $P_{(1-x1)}Q_{x1}$ with the volume fraction of $Vf_1$, a2 formed of $P_{(1-x2)}Q_{x2}$ with the volume fraction of $Vf_2$, and b formed of R with the volume fraction $Vf_3$, the concentration of said atom of interest contained in said polycrystalline compound semiconductor is calculated in a concentration calculation step with the expression {Concentration of the atom of interest contained in polycrystalline compound semiconductor=
($X1 Vf_1 + X2 Vf_2$) $100/(Vf_1+Vf_2)$ [atomic %]}.

17. A composition determining method for polycrystalline compound semiconductor using a spectroscopic ellipsometer according to claim 6, further comprising:

a spectrum measuring step for obtaining spectra $\Psi_E(\lambda_i)$ and $\Delta_E(\lambda_i)$ by measuring said polycrystalline compound semiconductor layer on a substrate which is to be measured with various wavelengths of incident light, which represent the change in polarization of said incident light and the reflected light for each wavelength $\lambda_i$; and a second step wherein processing up to said first step of said second analyzing stage described in claim 6 is performed for a plurality of measurement conditions (Zi) which can be anticipated, and the model with the minimal mean square error, or the model with the minimal mean square which is in a predetermined range between the predetermined minimal and maximal values of the film thickness, parameters of the dispersion formula, volume fraction, or incident angle, is selected from the results obtained for said plurality of measurement conditions, composition determining method for polycrystalline compound semiconductor using a spectroscopic ellipsometer, comprising:

a spectrum measuring step for obtaining spectra $\Psi_E(\lambda_i)$ and $\Delta_E(\lambda_i)$ by measuring said polycrystalline compound semiconductor layer with various wavelengths of incident light, which represent the change in polarization of said incident light and the reflected light for each wavelength $\lambda_i$; and a first analyzing stage including:
a first step for forming a plurality of models including said substrate with the complex refractive index of $(N_0(n_0, k_0))$ and layers with the complex refractive indexes of $(N_1(n_1, k_1))$, $(N_2(n_2, k_2))$, and so on, and with film thicknesses, wherein the complex refractive index of said polycrystalline compound semiconductor layer is calculated based upon an assumption that said polycrystalline compound semiconductor layer is formed of the mixture of crystalline compound semiconductor containing the atom of interest, and amorphous compound semiconductor containing said atom of interest, a second step for obtaining parameters of a dispersion formula for said unknown amorphous compound semiconductor by performing fitting with said film thicknesses and the volume fraction as variables, a third step for selecting the result with the minimal mean square error and the minimal volume fraction of said amorphous compound semiconductor from said fitting results, and a fourth step for selecting the result with the minimal mean square error and the minimal volume fraction of said amorphous compound semiconductor from said best results from a plurality of models.

18. A measuring method for a thin film on a substrate which is to be measured, using a spectroscopic ellipsometer, said method comprising:

a spectrum measuring step for obtaining spectra $\Psi_E(\lambda_i)$ and $\Delta_E(\lambda_i)$ by measuring a thin film on a substrate which is to be measured with various wavelengths of incident light, which represent the change in polarization of said incident light and the reflected light for each wavelength $\lambda_i$;

a modeling spectrum calculating step wherein a model including said substrate with $(N_0(n_0, k_0))$ and a first layer with $(d_1, N_1(n_1, k_1))$, is formed, and modeling spectra $\Psi_M(\lambda_i)$ and $\Delta_M(\lambda_i)$ are obtained based upon said model using reference data or a dispersion formula;

a comparative evaluating step wherein comparison is made between said measured spectra $\Psi_E(\lambda_i)$ and $\Delta_E(\lambda_i)$ and said modeling spectra $\Psi_M(\lambda_i)$ and $\Delta_M(\lambda_i)$, and the structure corresponding to said modeling spectra $\Psi_M(\lambda_i)$ and $\Delta_M(\lambda_i)$ satisfying predetermined evaluation criteria is determined as the measured result; and a modifying step wherein said model not satisfying said predetermined evaluation criteria is modified, and processing in said modeling spectrum calculating step and processing in said comparative evaluating step are performed again, wherein simulation spectra $\Psi_{Mk}(\lambda_i)$ and $\Delta_{Mk}(\lambda_i)$ are calculated with an incident angle $\phi_k$ as a parameter around a nominal incident angle $\phi_0$ used in said spectrum measuring step, in said modeling spectrum calculating step;

and wherein a comparison is made between said measured spectra $\Psi_E(\lambda_i)$ and $\Delta_E(\lambda_i)$ and said modeling spectra $\Psi_{Mk}(\lambda_i)$ and $\Delta_{Mk}(\lambda_i)$, and the structure corresponding to said modeling spectra $\Psi_{Mk}(\lambda_i)$ and $\Delta_{Mk}(\lambda_i)$ satisfying predetermined evaluation criteria is determined as the measured result in said comparative evaluating step.

19. A measuring method for a thin film on a substrate which is to be measured, using a spectroscopic ellipsometer, said method comprising:

a spectrum measuring step for obtaining spectra $\Psi_E(\lambda_i)$ and $\Delta_E(\lambda_i)$ by measuring a thin film on a substrate which is to be measured with various wavelengths of incident light, which represent the change in polarization of said incident light and the reflected light for each wavelength $\lambda_i$;

a modeling spectrum calculating step wherein a model including said substrate with $(N_0(n_0, k_0))$, a first layer with $(d_1, N_1(n_1, k_1))$, and a j-th layer with $(d_j, N_j(n_j, k_j))$, is formed, and modeling spectra $\Psi_M(\lambda_i)$ and $\Delta_M(\lambda_i)$ are obtained based upon said model using reference data or a dispersion formula;

a comparative evaluating step wherein comparison is made between said measured spectra $\Psi_E(\lambda_i)$ and $\Delta_E(\lambda_i)$ and said modeling spectra $\Psi_M(\lambda_i)$ and $\Delta_M(\lambda_i)$, and the structure corresponding to said modeling spectra $\Psi_M(\lambda_i)$ and $\Delta_M(\lambda_i)$ satisfying predetermined evaluation criteria is determined as the measured result; and a modifying step wherein said model not satisfying said predetermined evaluation criteria is modified, and processing in said modeling spectrum calculating step and processing in said comparative evaluating step are performed again, wherein simulation spectra $\Psi_{Mk}(\lambda_i)$ and $\Delta_{Mk}(\lambda_i)$ are calculated with an incident angle $\phi_k$ k as a parameter around a nominal incident angle $\phi_0$ used in said spectrum measuring step, in said modeling spectrum calculating step;

and wherein a comparison is made between said measured spectra $\Psi_E(\lambda_i)$ and $\Delta_E(\lambda_i)$ and said modeling spectra $\Psi_{Mk}(\lambda_i)$ and $\Delta_{Mk}(\lambda_i)$, and the structure corresponding to said modeling spectra $\Psi_{Mk}(\lambda_i)$ and $\Delta_{Mk}(\lambda_i)$ satisfying predetermined evaluation criteria is determined as the measured result in said comparative evaluating step.

20. A measuring method for a thin film using a spectroscopic ellipsometer according to claim 18, wherein evaluation of said model is performed with an evaluation criterion wherein mean square error of said measured spectra $\Psi_E(\lambda_i)$ and $\Delta_E(\lambda_i)$ and said modeling spectra $\Psi_M(\lambda_i)$ and $\Delta_M(\lambda_i)$ is obtained for each model, and the model with the minimal mean square error is determined to be the best model.

21. A composition determining method for a compound semiconductor layer wherein the surface of a compound semiconductor layer formed on a substrate is measured using a spectroscopic ellipsometer, and the composition ratios x and y of said compound semiconductor layer formed on said substrate are determined, said composition determining method comprising:

a spectrum measuring step for obtaining spectra $\Psi_E(\lambda_i)$ and $\Delta_E(\lambda_i)$ by measuring a thin film on a substrate which is to be measured with various wavelengths of incident light, which represent the change in polarization of said incident light and the reflected light for each wavelength $\lambda_i$;

a modeling spectrum calculating step wherein a model including said substrate with ($N_0(n_0, k_0)$) is formed, and modeling spectra $\Psi_M(\lambda_i)$ and $\Delta_M(\lambda_i)$ are obtained based upon said model;

a comparative evaluating step wherein comparison is made between said measured spectra $\Psi_E(\lambda_i)$ and $\Delta_E(\lambda_i)$ and said modeling spectra $\Psi_M(\lambda_i)$ and $\Delta_M(\lambda_i)$, and the structure corresponding to said modeling spectra $\Psi_M(\lambda_i)$ and $\Delta_M(\lambda_i)$ satisfying predetermined evaluation criteria is determined as the measured result (d, n, k, and the composition ratio are determined); and a modifying step wherein said model not satisfying said predetermined evaluation criteria is modified, and processing in said modeling spectrum calculating step and processing in said comparative evaluating step are performed again.

\* \* \* \* \*